(12) United States Patent
Iwata et al.

(10) Patent No.: US 7,846,731 B2
(45) Date of Patent: Dec. 7, 2010

(54) METHOD OF INTRODUCING NUCELIC ACID

(75) Inventors: Hiroo Iwata, Kyoto (JP); Koichi Kato, Kyoto (JP); Fumio Yamauchi, Kyoto (JP)

(73) Assignee: Kyoto University, Kyoto (JP)

( * ) Notice: Subject to any disclaimer, the term of this patent is extended or adjusted under 35 U.S.C. 154(b) by 809 days.

(21) Appl. No.: 10/572,920

(22) PCT Filed: Aug. 20, 2004

(86) PCT No.: PCT/JP2004/012004

§ 371 (c)(1), (2), (4) Date: May 5, 2006

(87) PCT Pub. No.: WO2005/035755

PCT Pub. Date: Apr. 21, 2005

(65) Prior Publication Data

US 2007/0059832 A1 Mar. 15, 2007

(30) Foreign Application Priority Data

Oct. 8, 2003 (JP) ............................ 2003-349343

(51) Int. Cl.
*C12N 15/87* (2006.01)
(52) U.S. Cl. .................. 435/461; 435/470; 435/471; 435/285.2
(58) Field of Classification Search .................. None
See application file for complete search history.

(56) References Cited

U.S. PATENT DOCUMENTS 4,441,972 A * 4/1984 Pohl ........................... 435/450
5,232,856 A * 8/1993 Firth ......................... 435/285.2

OTHER PUBLICATIONS

T. Yoshikawa et al., "Transfection microarray of human mesenchymal stem cells and on-chip siRNA gene knockdown", Journal of Controlled Release, vol. 96, pp. 227-232, 2004.
Pei, R. et al.; "Assembly of Alternating Polycation and DNA Multilayer Films by Electrostatic Layer-by-Layer Adsorption"; Biomacromolecules, American Chemical Society, US, vol. 2, No. 2, Mar. 8, 2001, pp. 463-468; XP002366101.
Raptis, L. et al.; "In Situ Electroporation of Large Numbers of Cells Using Minimal Volumes of Material"; Analytical Biochemistry, vol. 317, No. 1, Jun. 1, 2003, pp. 124-128; XP002404716.
Yamauchi F. et al.; "Spatially and Temporarily Controlled Gene Transfer by Electroporation into Adherent Cells on Plasmid DNA-loaded Electrodes"; Nucleic Acids Research 2004; vol. 32, No. 22 , Dec. 21, 2004; XP002404717.
Yamauchi F. et al.; "Layer-by-Layer Assembly of Poly(ethyleneimine) and plasmid DNA onto Transparent Indium-tin Oxide Electrodes for Temporally and Spatially Specific Gene Transfer"; Langmuir: The ACS Journal of Surfaces and Colloids; vol. 21, No. 18, Aug. 30, 2005; pp. 8360-8367; XP002404717.

* cited by examiner

*Primary Examiner*—James S Ketter
(74) *Attorney, Agent, or Firm*—Wenderoth, Lind & Ponack, L.L.P.

(57) ABSTRACT

The present invention relates to a method of introducing nucleic acids into cells by electroporation, comprising
the step (A) of loading nucleic acids to the surface of an electrode;
the step (B) of adhering cells on the obtained nucleic acid-loaded electrode surface; and
the step (C) of applying electric pulses to the adhering cells. According to this method, not only efficient introduction of a gene into cells but also gene introduction at desirable timing and at desirable sites can be performed without damaging the adhering cells.

22 Claims, 11 Drawing Sheets

Cell incubation time (hour) before applying an electric pulse
on the plasmid DNA-loaded electrode Cell incubation time (hour) before applying an electric pulse
on the plasmid DNA-loaded electrode Scale bar 200 μm Phase contrast    EGFP    DsRed 200 μm 1 mm

METHOD OF INTRODUCING NUCELIC ACID

This application is a U.S. national stage of International Application No. PCT/JP2004/012004 filed Aug. 20, 2004.

TECHNICAL FIELD

The present invention relates to a method of introducing a nucleic acid, and more specifically, relates to a method of introducing a nucleic acid into cells by electroporation.

BACKGROUND ART

A method of introducing genes into cells is utilized for elucidating gene function and the nature of proteins encoded by genes and for producing recombinant proteins voluminously. Further, the method of introducing genes into cells is also utilized for introducing a gene of objective enzymes or cytokines into the cells of a subject and producing an objective substance in the body by the genes, thereby to provide the treatment for diseases.

The sequencing of human genomic DNA has been nearly completed and the existence of genes with variously unknown functions is anticipated. Hereafter, the functional analysis of novel human genes is the great challenge in research, but a procedure which can excessively express and knockout genes exhaustively and at high throughput is necessary in order to carry out the functional analysis of genes which extend to several ten thousands of kinds.

Technology of introducing genes into cells is roughly classified into a biological method, namely an introduction method utilizing virus vectors derived from adenovirus, retrovirus and lentivirus, and an introduction method utilizing physical means such as a lipofection method (liposome method), an electroporation method (electric perforation method), a microinjection method and a particle gun method.

Among these, the method utilizing virus vectors is high in the efficiency of gene introduction, but there are drawbacks that the preparation of virus vectors is complicated and problem is found in safety. Although the lipofection method is high in safety, there are drawbacks that the efficiency of gene introduction is low and cell toxicity is strong, and the like.

The direct introduction methods such as a micro injection method and a particle gun method have drawbacks that cell damage is great, the optimization of conditions for efficient introduction of genes is troublesome, and specific technique and instruments are also required with respect to the technical operation.

Further, a conventional electroporation method has adopted a method of arranging a medium in which genes and cells are suspended, between electrodes such as parallel plates, applying electric pulses between both electrodes to produce small pores in the cell membrane and introducing foreign genes into the cells before they are restored (non-patent literatures 1: EMBO Journal, 1982, Vol. 1, pages 841 to 845; and non-patent literature 2: Bioelectrochem. & Bioenerg., 1999, Vol. 48, pages 3 to 16). Although this method is high in the efficiency of introducing genes, there are drawbacks that the cell damage is great, and the timing and the site of introducing genes are hardly selected freely, etc.

Furthermore, there has been recently developed a transfectional array by which cells are cultivated on a glass substrate on which expression plasmids are printed and genes are introduced into the cells by the lipofection method, in order to analyze the function of genes at high throughput (non-patent literature 3: Nature 2001, Vol. 411, pages 107 to 110). Since this method uses the lipofection method for transfection, the above-mentioned drawbacks caused by the lipofection method still exist.

On the other hand, an alternate adsorption method is reported as a method of immobilizing biological molecules such as nucleic acids and proteins on the surface of a substrate in the state where its activity is kept (non-patent literature 4: Biosensors & Bioelectronics, 1994, Vol. 9, pages 677 to 684). This method is a method of alternately adsorbing polymers with different electrostatic charges on a substrate and sequentially laminating polymer thin films by electrostatic interactions (formation of polyelectrolyte complex), but an example applied for a method of introducing genes has not been reported.

DISCLOSURE OF THE INVENTION

Problems to be Solved by the Invention

It is an object of the present invention to provide a method of introducing genes by solving the problems of a conventional electroporation, and more specifically, to provide a method wherein not only efficient introduction of genes into cells can be accomplished but also gene introduction can be performed at desirable timing and at desirable site, without damaging the cells. Further, it is another object of the present invention to provide a method capable of carrying out the above-mentioned gene introduction using an electrode substrate which can provide good observation environment in the microscopic observation of cells.

Means for Solving the Problems

The present inventors have made attempts to improve a method of introducing genes by a conventional electroporation, and as a result, have found that by loading nucleic acids onto an electrode surface, allowing cells to adhere to the obtained nucleic acid-loaded electrode surface, and applying electrical pulses to the adhering cells, not only efficient introduction of genes into cells but also gene introduction at desirable timing and at desirable site can be performed, without damaging the cells. Further, the present inventors have studied methods much more and as a result, have found that when a transparent semiconductor electrode is used as the electrode, themicroscopic observation of cells can be carried out well. The present inventors have completed the present invention based on the above-mentioned findings.

Namely, the present invention is (1) a method of introducing a nucleic acid into cells by electroporation, comprising the step (A) of loading a nucleic acid onto the surface of an electrode;

the step (B) of adhering cells onto the surface of the obtained nucleic acid loaded electrode; and the step (C) of applying electric pulses to the adhering cells, (2) a method of introducing a nucleic acid into cells by electroporation, comprising the step (a) of providing an electrode with a cationic surface;

the step (b) of adsorbing and loading a nucleic acid onto the cationic surface of an electrode;

the step (c) of adhering cells to the surface of the nucleic acid-loaded electrode obtained in the step (b); and the step (d) of applying electric pulses to the cells, (3) the method according to the above (2), wherein the electrode with a cationic surface is an electrode with a cationic surface on which a monolayer of a thiol compound, a disulfide compound or a sulfide compound having an anionic functional group at the terminal is formed and a cationic polymer is adsorbed onto the surface of the monolayer, (4) the method according to the above (2), wherein the electrode with a cationic surface is an electrode on which a monolayer of a thiol compound, a disulfide compound or a sulfide compound or a silanising agent having a cationic functional group at the terminal is formed, an anionic polymer is adsorbed onto the surface of the monolayer and a cationic polymer is further adsorbed onto its surface, (5) the method according to the above (2), wherein the electrode with a cationic surface is a transparent electrode on which a cationic polymer is adsorbed, (6) the method according to the above (2), wherein the step (b) is carried out by directly adsorbing nucleic acids on the cationic surface of an electrode only once, or adsorbing alternately nucleic acid and cationic polymer onto the surface in the order of the nucleic acid, cationic polymer and nucleic acid by an alternate adsorption method, (7) the method according to the above (3) or (4), wherein the electrode is an electrode made of a metal selected from platinum, gold and aluminum, (8) the method according to the above (3) or (4), wherein the electrode is a gold electrode substrate, (9) the method according to the above (8), wherein the gold electrode is a glass substrate or a transparent plastic substrate on which gold is deposited,

(10) the method according to the above (5), wherein the transparent electrode is a glass substrate or a transparent plastic substrate on which indium-tin oxide, indium oxide, aluminum-doped zinc oxide or antimony-doped tin oxide is deposited.

(11) the method according to the above (5), wherein the transparent electrode is a glass substrate or a transparent plastic substrate on which indium-tin oxide is deposited,

(12) the method according to the above (3), wherein the thiol compound having an anionic functional group at the terminal is a thiol compound indicated by the formula (1):

$$R^1(CH_2)_n\text{—SH} \quad (1)$$

(wherein $R^1$ represents an anionic functional group and n represents an integer of 1 to 40),

(13) the method according to the above (12), wherein $R^1$ is a group selected from carboxylic acid, phosphoric acid, sulfonic acid group and phosphonic acid,

(14) the method according to the above (12), wherein the thiol compound represented by the formula (1) is mercaptoalkanoic acid selected from 11-mercaptoundecanoic acid, 8-mercaptooctanoic acid and 15-mercaptohexadecanoic acid,

(15) the method according to the above (3), (4) or (5), wherein the cationic polymer is a polymer selected from polyethyleneimine, polyallylamine, polyvinylamine, polyvinylpyridine, aminoacetalized poly(vinyl alcohol), acrylic or methacrylic polymer having primary to quaternary amine at the terminal of a side chain, acid-treated gelatin, protamine, polylysine, polyornithine, polyarginine, chitosan, DEAE-cellulose, DEAE-dextran and polyamidoamine dendrimer.

(16) the method according to the above (4), wherein the thiol compound having a cationic functional group at the terminal is a thiol compound represented by the formula (2):

$$R^2(CH_2)_n\text{—SH} \quad (2)$$

(wherein $R^2$ represents a cationic functional group and n represents an integer of 1 to 40),

(17) the method according to the above (16), wherein $R^2$ is an amino group,

(18) the method according to the above (1) or (2), wherein the nucleic acid is DNA, RNA, antisense nucleic acid, siRNA or expression vector thereof,

(19) the method according to the above (1) or (2), wherein the nucleic acid is DNA or a part thereof which encodes a protein,

(20) the method according to the above (1), wherein the step (B) is carried out by incubating cells on the nucleic acid-loaded electrode,

(21) the method according to the above (2), wherein the step (c) is carried out by incubating cells on the surface of the nucleic acid-loaded electrode,

(22) the method according to the above (1), wherein the step (C) is carried out by providing a counter electrode facing to the nucleic acid-loaded electrode on which cells adhere, and generating electric pulses between both electrodes,

(23) the method according to the above (2), wherein the step (d) is carried out by providing a counter electrode facing to the nucleic acid-loaded electrode on which cells adhere, and generating electric pulses between both electrodes, and

(24) the method according to the above (2), wherein the electrode with a cationic surface is an electrode having micropatterned surface.

Further, the present invention is

(25) an electrode with a cationic surface wherein the monolayer of a thiol compound, a disulfide compound or a sulfide compound having an anionic functional group at the terminal is formed and a cationic polymer is adsorbed onto the surface of the monolayer, and

(26) an electrode with a cationic surface, wherein the monolayer of a thiol compound represented by the formula (1):

$$R^1(CH_2)_n\text{—SH} \quad (1)$$

(wherein $R^1$ represents an anionic functional group and n represents an integer of 1 to 40)

is formed on the surface of a gold electrode prepared by depositing gold onto a glass substrate and a cationic polymer is adsorbed onto the surface of the monolayer.

Effect of the Invention

The present invention provides a method of introducing a nucleic acid into cells by electroporation, by which not only efficient introduction of nucleic acids into cells but also nucleic acid introduction at desirable timing and at desirable site on an electrode can be performed, without damaging the cells.

DESCRIPTION OF CODES

Figure 1:
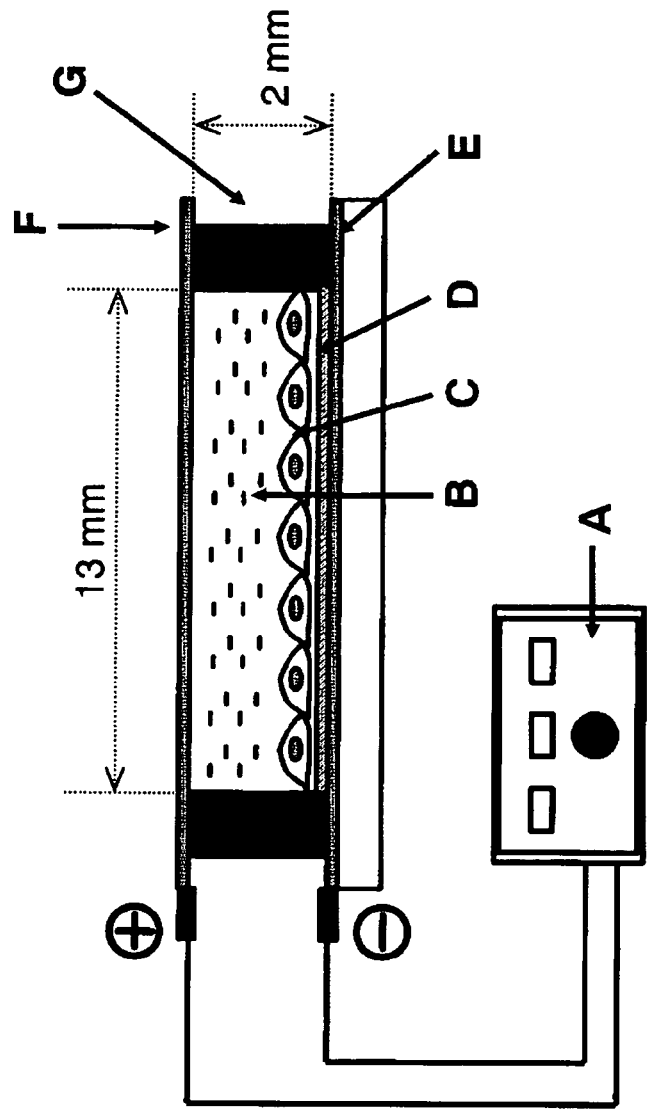
FIG. 1 shows a set up for electroporation of adherent cells on the nucleic acid-loaded gold electrode and electric pulsing system.

The meanings of the symbols in FIG. 1 are as follows.
A: Electroporator
B: Electroporation buffer
C: Cell
D: Nucleic acid-cationic polymer composite layer
E: Gold thin film electrode (cathode)
F: Gold electrode (anode)
G: Silicone spacer

BEST MODE FOR CARRYING OUT THE INVENTION

An aspect of the present invention is a method of introducing a nucleic acid into cells by electroporation, comprising
a step (A) of loading a nucleic acid onto the electrode surface;
a step (B) of adhering cells on the obtained nucleic acid-loaded electrode surface; and
a step (C) of applying electric pulses to the adherent cells.

The respective steps mentioned above are sequentially illustrated below.

Step (A):
In order to load a nucleic acid on an electrode, there can be adopted, for example,
(A1) a method of providing an electrode with a cationic surface and then adsorbing a nucleic acid on the cationic surface of the electrode,
(A2) a method of providing an electrode with a cationic surface, then alternately adsorbing a nucleic acid and a cationic polymer on the cationic surface of the electrode and forming a multilayer such as cationic polymer-nucleic acid-cationic polymer-nucleic acid, and the like.

(Presentation of Cationic Surface Electrode Substrate)

The electrode with a cationic surface may be selected from those in which the surface of an electrode has positive charge and the example of such electrode includes
(a1) an electrode on which a monolayer of a thiol compound, a disulfide compound or a sulfide compound having an anionic functional group at the terminal is formed and a cationic polymer is adsorbed onto the surface of the monolayer,
(a2) an electrode on which a monolayer of a thiol compound, a disulfide compound or a sulfide compound or a silanising agent having a cationic functional group at the terminal is formed, an anionic polymer is adsorbed onto the surface of the monolayer, and a cationic polymer is further adsorbed onto its surface,
(a3) an electrode on which a cationic polymer is adsorbed onto the surface, and the like.

The electrode with a cationic surface mentioned above (a1) can be produced, for example, by 1) forming a monolayer of a thiol compound, a disulfide compound or a sulfide compound having an anionic functional group at the terminal on the surface of an electrode substrate and 2) adsorbing a cationic polymer on the surface of the monolayer.

Further, the electrode with a cationic surface mentioned above (a2) can be produced, for example, by 1) forming a monolayer of a thiol compound, a disulfide compound, a sulfide compound or a silanising agent having a cationic functional group at the terminal on the surface of an electrode substrate, 2) adsorbing an anionic polymer on the surface of the monolayer, and then 3) adsorbing a cationic polymer on the surface of the anionic polymer.

Further, the electrode with a cationic surface mentioned above (a3) can be produced, for example, by adsorbing a cationic polymer on the surface of an electrode.

An electrode is supported by a substrate such as a plate, a chip (including a micro chip), an array and the like. The base materials composing these are not specifically limited so far as they are an insulating material capable of supporting the electrode, and for example, there can be used inorganic insulating materials such as glass, mica, quartz, alumina, sapphire, forsterite, silicon carbide, silicon oxide and silicon nitride; organic insulating materials such as polyethylene, polypropylene, polyisobutylene, poly(ethylene terephthalate), unsaturated polyester, fluorine containing resin, poly(vinyl chloride), poly(vinylidene chloride), poly(vinyl acetate), poly(vinyl alcohol), poly(vinyl acetal), acrylic resin, polyacrylonitrile, polystyrene, acetal resin, polycarbonate, polyamide, phenol resin, urearesin, epoxyresin, melamine resin, styrene-acrylonitrile copolymer, acrylonitrile-butadiene-styrene copolymer, poly(phenylene oxide) and polysulfone.

Among these, the base material of the substrate in the electrode with a cationic surface mentioned above (a1) and (a2) is preferably inorganic insulating materials such as glass, mica, quartz, alumina, sapphire, forsterite, silicon carbide, silicon oxide and silicon nitride, or a transparent plastic. The base material of the substrate in the electrode with a cationic surface mentioned above (a3) is preferably glass or a transparent plastic, and glass is particularly preferable. The above-mentioned transparent plastic is not specifically limited so far as it is a transparent polymer material having no self-fluorescence and may be a known material. As the transparent plastic, for example, the above-mentioned organic materials and the like are exemplified, but among these, poly(ethylene terephthalate) is preferable.

On the other hand, the electrode is not particularly limited so far as it is an electrode which can be an electrode in the electroporation method, but an electrode made of a metal material such as platinum, gold, and aluminum is preferable. Further, a transparent electrode is preferably mentioned for facilitating the microscopic observation of cells. The transparent electrode includes indium-tin oxide (ITO: $In_2O_3$—$SnO_3$), aluminum-doped zinc oxide (ZnO), antimony-doped tin oxide ($SnO_3$) and the like, and indium-tin oxide is particularly preferable.

The preferable example of the electrode substrate comprising the above-mentioned "substrate" and "electrode" includes those in which a metal electrode such as platinum, gold or aluminum or a transparent electrode is provided on one side of a glass substrate, a plastic substrate or a mica substrate. The preferable example of the former includes those in which a gold electrode is provided on one side of a glass substrate, a mica substrate or a transparent plastic substrate, and the preferable example of the latter includes those in which an indium-tin oxide transparent electrode is provided on one side of a transparent substrate such as a glass substrate and a transparent plastic substrate.

It may be carried out according to the known methods to provide an electrode on one side of a substrate and, for example, a method of using a known procedure that the above-mentioned metal is heated or/and pressed on an inorganic insulating substrate to be united is mentioned. Further, a vacuum deposition method, a spattering method, an ion injection method, a plating method and the like other than the above-mentioned method are also mentioned.

As the thiol compound having an anionic functional group at the terminal which is used for forming a monolayer on the surface of an electrode, for example, a thiol compound represented by the general formula (1) below:

$$R^1(CH_2)_n\text{—}SH \tag{1}$$

(wherein the symbols have the same meaning as defined above) is mentioned. The preferable example of the compound (1) includes those in which $R^1$ for an anionic functional group is carboxylic acid, phosphoric acid, sulfonic acid or phosphonic acid, and n is 1 to 40, preferably 7 to 18.

Further, in place of the thiol compound (1), there can also be used a disulfide compound or a sulfide compound represented by the general formula (1A) or (1B) below:

$$R^1(CH_2)_n\text{—}S\text{—}S\text{—}(CH_2)_m\text{—}R^1 \tag{1A}$$

$$R^1(CH_2)_n\text{—}S\text{—}(CH_2)_m\text{—}R^1 \tag{1B}$$

(wherein $R^1$ and n have the same meaning as defined above and m represents an integer of 1 to 40). Although the disulfide compound or the sulfide compound may be a symmetric type or an asymmetric type, a symmetric type is preferable because a uniform monolayer is formed.

The specific example of the preferable compound (1) or its disulfide or sulfide compound includes, for example, 11-mercaptoundecanoic acid, 8-mercaptooctanoic acid and 15-mercaptohexadecanoic acid, 10-carboxydecyl disulide and the like.

Further, as the thiol compound having a cationic functional group at the terminal which is used for forming a monolayer on the surface of an electrode, there is exemplified, for example, a thiol compound represented by the following general formula (2):

$$R^2(CH_2)_n\text{—}SH \tag{2}$$

(wherein $R^2$ represents a cationic functional group, and n has the same meaning as defined above). As the cationic functional group represented by $R^2$, there is exemplified, for example, an amino group; and n is an integer of 1 to 40, preferably 7 to 18.

Further, in place of the thiol compound (2), there may be used a disulfide compound or a sulfide compound represented by the following general formula (2A) or (2B):

$$R^2(CH_2)_n\text{—}S\text{—}S\text{—}(CH_2)_m\text{—}R^2 \tag{2A}$$

$$R^2(CH_2)_n\text{—}S\text{—}(CH_2)_m\text{—}R^2 \tag{2B}$$

(wherein $R^2$ and n have the same meaning as defined above, and m represents an integer of 1 to 40). Although the disulfide compound or the sulfide compound may be a symmetric type or an asymmetric type, it is preferable to use a symmetric type because it can form a uniform monolayer.

The specific example of the preferable compound (2) or its disulfide or sulfide compound includes preferably, for example, 11-amino-1-undecanethiol and the like.

As the silanising agent having a cationic functional group at the terminal which is used for forming a monolayer on the surface of an electrode, there is exemplified, for example, a silane compound represented by the general formula (3) below:

$$R^2(CH_2)_p\text{—}Si(OR)_3 \tag{3}$$

(wherein $R^2$ has the same meaning as defined above, p represents an integer of 1 to 40, and OR represents an alkoxy group). As the cationic functional group represented by $R^2$, for example, an amino group is mentioned. An integer of 1 to 40, preferably 7 to 18, is mentioned as p, and a lower alkoxy group having a carbon number of 1 to 6, preferably 1 to 3, is mentioned as OR.

It may be carried out according to conventional methods to form a monolayer on the surface of an electrode. For example, an electrode substrate is immersed in the solution of a thiol compound (the formula 1 or 2), its disulfide compound (the formula 1A or 2A), the sulfide compound (the formula 1B or 2B), or the silanising agent (3), thereby to form a monolayer with high density and high orientation on the electrode.

When a thiol compound (1) having an anionic functional group at the terminal or its disulfide compound or sulfide compound (1A or 1B) is used as the thiol compound, an electrode with the cationic surface mentioned above (a1) is obtained by adsorbing a cationic polymer on the surface of the monolayer of these compounds.

The "cationic polymer" used herein may be a cationic polymer which is adsorbed to the surface of the monolayer by electrostatic interactions (for example, ionic bond) with the monolayer formed on the surface of an electrode. Examples of such cationic polymers include a polyethyleneimine, polyallylamine, polyvinylamine, polyvinylpyridine, aminoacetalized poly(vinyl alcohol), acrylic or methacrylic polymer (for example, poly(N,N-dimethylaminoethylmethacrylate) and the like) having primary to quaternary amine at the terminal of the side chain, acid treated gelatin, polylysine, polyornithine, polyarginine, protamine, chitosan, DEAE-cellulose, DEAE-dextran and polyamidoamine dendrimer (cationic dendrimer) and the like. Among these, a polyethyleneimine and polyallylamine are particularly preferable.

The average molecular weight of the cationic polymer is 500 to 5000000 and preferably 600 to 100000. For example, in case of a polyethyleneimine, its average molecular weight is preferably 200 to 25000 and preferably 500 to 10000 in particular. Further, in case of a polyallylamine, its average molecular weight is preferably 500 to 150000 and preferably 1000 to 70000 in particular.

The adsorption of the cationic polymer on the surface of a monolayer can be carried out by bringing the solution of a cationic polymer on the surface of a monolayer. For example, it can be preferably carried out by adding a solution in which the cationic polymer was dissolved in an appropriate buffer (for example, phosphate buffered saline), on the surface of the monolayer and leaving it at room temperature. The concentration of the cationic polymer is not particularly limited, but preferably 0.1% to 10%. Thus, the monolayer and the cationic polymer are adsorbed by ionic interactions, and an electrode with the cationic surface mentioned above (a1) is provided.

When the thiol compound (2) or its disulfide or sulfide compound (2A or 2B) having a cationic functional group at the terminal is used as a thiol compound, or when the silanising agent (3) having a cationic functional group at the terminal is used as a silanising agent, an anionic polymer is firstly adsorbed onto the surface of the monolayer of these compounds.

The "anionic polymer" used herein may be an anionic polymer which is adsorbed to the surface of the monolayer by electrostatic interactions (for example, ionic bond) with a monolayer formed on the surface of an electrode. Examples of such anionic polymers include synthetic polymers such as poly(acrylic acid), poly(methacrylic acid), poly(styrene sulfonic acid) poly(2-acrylamido-2-methylpropanesulfonic acid), and natural polymers such as arginic acid, hyaluronic acid, condroitin sulfate and alkali-treated gelatin.

The adsorption of the anionic polymer on the surface of a monolayer can be carried out by bringing the solution of an anionic polymer into contact with the surface of the monolayer. For example, it can be preferably carried out by adding a solution in which the anionic polymer was dissolved in an appropriate buffer (for example, phosphate buffered saline), on the surface of the monolayer and leaving it alone at room temperature.

Then, an electrode with a cationic surface mentioned above (a2) is obtained by adsorbing a cationic polymer on the surface of the adsorbed anionic polymer. As the cationic polymer used herein, the same cationic polymer as those mentioned above can be used, and adsorption can be carried out in a similar manner to that mentioned above.

Further, for example, when the above-mentioned transparent electrode such as indium-tin oxide and indium oxide is used as an electrode, the electrode with a cationic surface mentioned above (a3) wherein a cationic polymer is adsorbed onto the surface of the electrode is obtained by treating the surface of the electrode substrate with the cationic polymer. As the cationic polymer used herein, the same cationic polymer as above can be used, and treatment by the cationic polymer can be preferably carried out by adding the solution of a cationic polymer on the surface of an electrode substrate and leaving it alone at room temperature.

(Loading of Nucleic Acid on an Electrode with a Cationic Surface)

A nucleic acid-loaded electrode is obtained by loading the nucleic acids on the cationic surface of an electrode provided as described above.

The "nucleic acid" used in the present invention may be polynucleotide or oligonucleotide, and may be DNA or RNA. DNA may be a plasmid DNA, cDNA, genomic DNA or synthetic DNA. The "nucleic acid" includes DNA derivatives and RNA derivatives. The derivative means a nucleic acid having phosphorothioate bond or a nucleic acid in which chemical modification is carried out at the phosphoric acid portion, sugar portion and base portion of the internucleotide for preventing digestion by enzyme.

The "nucleic acid" includes plasmid DNA which encodes a protein having biological activity effective in treating or improving disease symptom, plasmid DNA which encodes a protein inducing immune reaction which is effective in preventing, treating or improving disease symptom, and a part of these DNAs.

The "nucleic acid" includes also antisense nucleic acid. The "antisense nucleic acid" is DNA molecule or RNA molecule which is complementary to at least one portion of specific mRNA molecule and is hybridized with corresponding mRNA by being introduced into cells, thereby to form double-stranded molecule. Since the cell does not translate double-stranded mRNA, the antisense nucleic acid interferes with the translation of the RNA. The "nucleic acid" further includes siRNA (small interfering RNA provoking RNA interference). Further, the "nucleic acid" includes expression vectors for the antisense nucleic acid and siRNA.

When the nucleic acid is plasmid DNA encoding a protein, a plasmid constructed so as to express genetic code in cells upon introduction of the nucleic acid into cells is preferable, and it contains segments required for the expression of objective gene such as promoter. Further, when it is required to confirm whether or not the objective gene is introduced into the cell, DNA further including reporter gene in addition to the objective gene may be desirable.

The size of the "nucleic acid" is not particularly limited, but in general, it is 10 bp to 200 kbp and preferably 15 bp to 100 kbp.

The loading of a nucleic acid on the cationic surface of an electrode can be carried out by bringing the solution of nucleic acids into contact with the cationic surface of an electrode and, for example, it can be preferably carried out by adding a solution in which nucleic acids were dissolved in an appropriate buffer (for example, phosphate buffered saline), to the cationic surface of an electrode and leaving it at room temperature. Unadsorbed nucleic acids can be removed by rinsing the surface of the electrode with an appropriate buffer (for example, phosphate buffered saline). Thus, a nucleic acid-loaded electrode substrate is obtained.

Further, a nucleic acid-loaded electrode can also be obtained by alternately adsorbing nucleic acids and cationic polymer on the cationic surface of an electrode in the order of nucleic acid, cationic polymer and nucleic acid. Here, the alternate adsorption of the nucleic acid and the cationic polymer which are carried out can be performed in a similar manner as above.

Step B

The present step is a step of adhering cells to the surface of a nucleic acid-loaded electrode obtained above.

The "cell" used in the present invention may be any cell derived from organisms so far as it is adhesive, and for example, may be arbitrary kind (for example, bacteria, yeast) or multicellular organisms (for example, animals such as vertebrate, invertebrate), plants (for example, monocotyledon, dicotyledon) and the like. For example, there are used cells derived from vertebrate (for example, hagfishes, lamperns, chondrichtian, osteichthyes, amphibian, reptile, aves, mammals and the like). More specifically, there are used cells derived from mammals (for example, monotreme, marsupial, edentate, dermoptera, chiropteran, carnivore, insectivore, proboscidean, perissodactyla, artiodactyla, tubulidentata, pholidota, sirenia, cetacean, primates and the like). In one embodiment, cells derived from primates (for example, chimpanzee, macaca and human) and cells derived from human are used in particular. The specific example of human origin cells includes, for example, human origin established cell line such as human cervical cancer cell (HeLa); human origin primary cultured cell such as human fetal kidney cell, human umbilical vein endothelial cell, human vascular endothelial cell, human arterial smooth muscle cell, human hepatocyte, human fibroblast, human corneal epithelial cell and human corneal endothelial cell; stem cell from human such as mesenchymal stem cell, embryonic stem cell and neural stem cell.

The method of adhering cells on the surface of a nucleic acid-loaded electrode is not particularly limited, and for example, it can be carried out by adding a cell suspension on the electrode, or suspending cells in an appropriate culture medium, adding dropwise the obtained cell suspension on the electrode and incubating it under conditions optimized for the cells. However, it is preferable to carry out the cultivation of cells on the nucleic acid-loaded electrode from the viewpoints of the efficiency of transfection and the restriction of the transfected sites in a cell population. By culturing the cells, they adhere to proliferate on the surface of the electrode. Non-adhered cells are preferably removed before applying electric pulses. The removal of non-adhered cells can be carried out, for example, by exchanging the culture medium with an appropriate buffer.

Step C

The application of electric pulses to the cells can be carried out by placing an electrode of a nucleic acid-loaded electrode (called as a first electrode) onto which cells adhere, providing a counter electrode (called as a second electrode) facing to the cells on the first electrode, and generating electric pulse between the first and second electrodes using an electroporator. At this time, although the electric pulse may be generated by either of alternate current or direct current, it is preferably generated by direct current in general.

When electric pulses are generated with direct current, the first electrode with loaded nucleic acids is used as cathode (−), and the second electrode is set as anode (+), or vice versa. It is preferable that the first electrode is set as cathode (−) and the second electrode is set as anode (+). The material of the second electrode is not particularly limited so far as it is electroconductive, but includes metals such as gold, platinum, copper, aluminum, stainless steel, tungsten, titanium, cobalt-chromium alloy, cobalt-chromium-molybdenum alloy (vitallium), or transparent electrode materials such as ITO (indium-tin oxide) and indium oxide.

As the condition of electric pulsing, field strength, duration of an electric pulse, number of pulse application and the like may be suitably selected depending on the kind of electrode materials, cells, nucleic acids to be introduced, cationic polymers on a substrate and the like. Usually, field strength is 10 to 500 V/cm and preferably 25 to 300 V/cm, duration of an electric pulse is 1 to 99 msec and preferably 1 to 50 msec, and the number of pulse application is 1 to 99 and preferably 1 to 5, but they are not limited to these.

The timing of applying electric pulse is not particularly limited and can be suitably selected. Namely, after cells are seeded on the nucleic acid-loaded electrode, incubated and adhered to the substrate, electric pulses should not always be applied immediately but can be applied at any time so far as it is within about 4 to 5 days after cell seeding. The nucleic acid is efficiently introduced into cells by application of the electric pulse.

FIG. 1 shows an arrangement of an electric pulsing setup with the nucleic acid-loaded electrode, used for carrying out the above-mentioned method of the present invention. The details of the present invention are illustrated using the drawing. For example, a gold thin film electrode (E) is formed on the surface of a glass substrate. A nucleic acid-cationic polymer composite layer (D) is formed on the electrode, and cells (C) are adhered to the surface of the layer. Further, the cells are partitioned, for example, by silicone spacer (G), and the well is filled with an electroporation buffer (B). A gold electrode (F) which is a counter electrode is placed on a silicon spacer (G) in parallel to the bottom electrode with cells, (E). The first electrode (E) and the second electrode (F) are connected to an electroporator (A) which generates electric pulses (A). In the present example, a distance between the first electrode (E) and the second electrode (F) is set as 2 mm and the area of wells is set as 13×13 mm$^2$. With respect to the polarity of an electric pulse, the first electrode (E) is set as cathode (−) and the second (F) is set as anode (+). The nucleic acid (DNA) is introduced into cells (C) by generating an electric pulse with the electroporator (A).

As another aspect of the present invention, the above-mentioned nucleic acid introduction method can be carried out using a substrate having micropatterned surface. The micro-patterning can be carried out by a known method. The nucleic acid-loaded electrode which is micro-patterned can be prepared by partitioning the cationic surface of an electrode with an appropriate means, and by loading multiple kinds of nucleic acids separately into each partition. Further, the surface of an electrode substrate is treated with an organic silane compound (for example, octadecyltriethoxysilane) or an alkanethiol to form their self-assembled monolayer, overlaid with a photo mask, irradiated with ultraviolet light to decompose the self-assembled monolayer to obtain a micro-patterned electrode substrate; therefore the nucleic acids can be arrayed using the substrate. Accordingly, when the present invention is carried out using the above-mentioned micro-patterned nucleic acid-loaded electrode, the sites where nucleic acids are introduced can be restricted.

The present invention is further explained below by way of Examples, but it is construed that the technical scope of the present invention is not limited by these Examples.

EXAMPLE 1

An electrode with a cationic surface was prepared for electrostatically adsorbing DNA. Firstly, a monolayer of a thiol compound (11-mercaptoundecanoic acid, manufactured by Sigma-Aldrich Co.) having a carboxyl group at the terminal was formed on a glass plate on which a gold thin film was deposited on one side. A phosphate buffered saline (pH=7.4) containing polyethyleneimine having an average molecular weight of 800 (hereinafter, referred to as PEI800, manufactured by Aldrich Co., Ltd.) at a concentration of 1% was added on the monolayer and kept at room temperature for 30 min. The surface of the substrate obtained was adequately rinsed with water and dried under nitrogen gas to obtain a gold electrode with a cationic surface.

Then, a silicone spacer (inner area: 1.3×1.3 cm$^2$ and height: 2 mm) sterilized with ethanol was fixed to the cationic surface of the gold electrode obtained above. Then, phosphate buffered saline (pH=7.4) containing 0.05 mg/ml plasmid DNA that encoded green fluorescent protein (pEGFP-C1, manufactured by Clontech Laboratories Inc.) was added to the cationic surface of the gold electrode in the silicone spacer and kept at room temperature for 2 hours to electrostatically adsorb DNA onto the surface. The surface was adequately rinsed with phosphate buffered saline in order to remove DNA which was not adsorbed, thereby to obtain a DNA-loaded gold electrode substrate.

Cells derived from human embryonic kidney (HEK293: obtained from Human Science Foundation) were suspended in serum containing culture medium (composition of culture medium: minimum essential culture medium (MEM) (Gibco Life Technology), 10% fetal bovine serum, 100 units/ml penicillin, 0.1 mg/ml streptomycin), and the suspension was plated onto the surface of the DNA-loaded gold electrode. The cells were incubated at 37° C. under 5% CO$_2$ atmosphere to adhere to the electrode surface. After 24 hours, the culture medium was exchanged with phosphate buffered saline (pH=7.4) at 4° C. to remove cells which did not adhere, the fresh phosphate buffered saline was again added to the surface. Then, a glass substrate on which a gold thin film was deposited on one side was immobilized on the silicone spacer as the second electrode. Their arrangement is shown in FIG. 1.

Then, the DNA-loaded gold electrode was set as cathode (−) and the second electrode was set as anode (+). They were connected to a high voltage pulse generation device (Electrosquarereportor T820, manufactured by BTX Division of Genetronics Inc.) and electric pulse was applied under the conditions of the field strength of 75 V/cm, a pulse duration of 10 msec and the number of pulse application of 1 to carry out electroporation. After pulse application, the cells were incubated at room temperature for 5 minutes, then the phosphate buffered saline in the wells was exchanged with serum-containing culture medium which was previously warmed at 37° C., and cell culture was carried out at 37° C. under atmosphere of 5% CO$_2$.

Analysis of transient expression of introduced gene was carried out 48 hours after electroporation. Cells emitting green fluorescence due to expression of green fluorescent protein (EGFP) were counted under a fluorescence microscope and transfection efficiency was determined as the number of EGFP positive cells per total number of cells.

Figure 2:
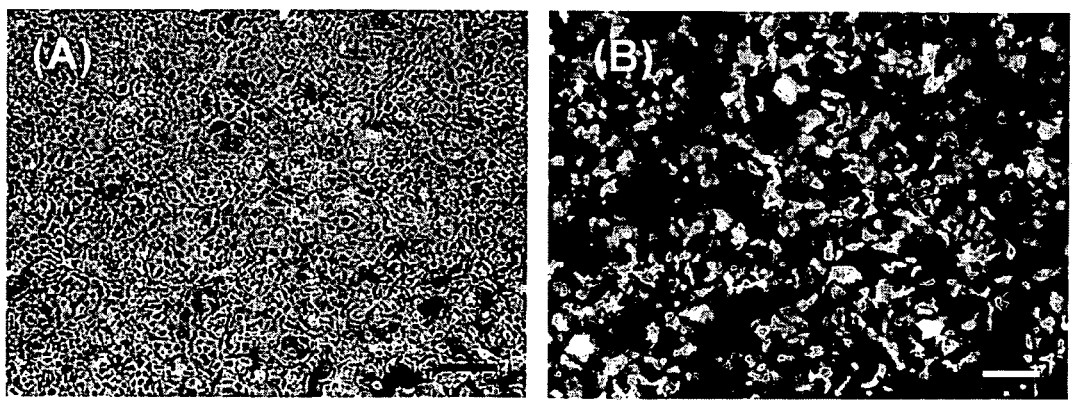
FIG. 2 shows (A) phase contrast and (B) fluorescence microphotographs of HEK293 cells 48 hours after an electric pulse (an field strength of 75 V/cm, a pulse duration of 10 msec and a pulse number of 1) was applied. Scale bar: 200 μm

FIG. 2 shows (A) phase contrast and (B) fluorescence microphotographs of HEK293 cells 48 hours after electroporation. As can be seen from the photographs, the cells on the surface of the electrode expressed EGFP without appreciable damage. The percentage of EGFP positive cells, namely the transfection efficiency was 80%. This result clearly indicates that the procedure of the present invention is a method that allows efficient introduction of genes.

EXAMPLE 2

Figure 3:
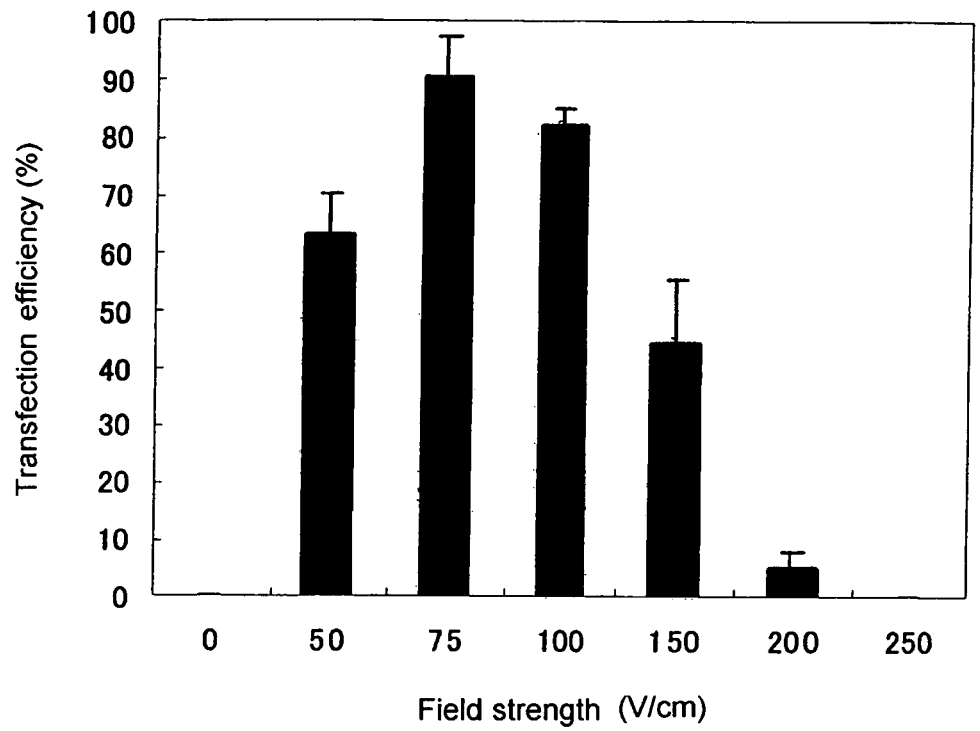
FIG. 3 is a bar graph showing the effect of field strength on the transfection efficiency.
Figure 4:
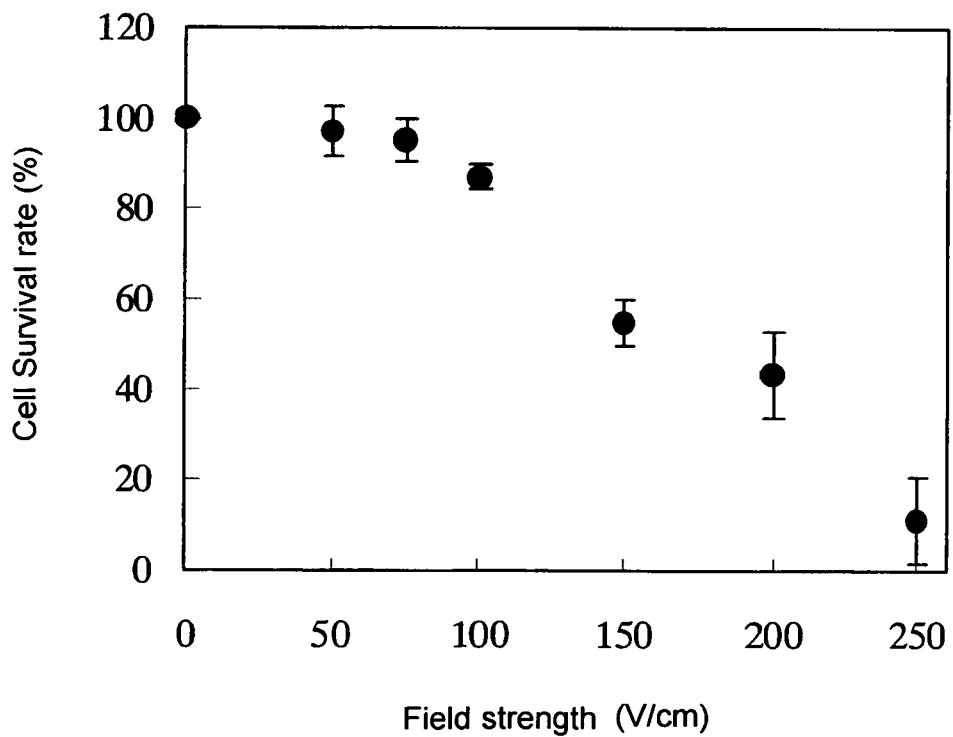
FIG. 4 is a diagram showing the relationship between cell survival rate and field strength.

In a similar manner to Example 1, HEK293 cells were seeded on the DNA-loaded gold electrode to adhere. Then electric pulse was applied to the cells to carry out electroporation. At that time, the voltage of electric pulse was changed and the effect of field strength on the transfection efficiency was studied. Further, conditions for pulse application other than voltage was the same as Example 1 (a pulse duration of 10 msec and the pulse number of 1). The transfection efficiency was evaluated as percent EGFP-positive cells 48 hours after the application of an electric pulse. The result is shown in FIG. 3. Further, the effect of field strength for cell survival rate was simultaneously studied. The cell survival rate was evaluated by a trypan blue dye exclusion method, wherein the cells were treated with trypsin 3 hours after the application of electric pulse to recover the cells. Namely, the number (number of living cells) of cells which were not stained with trypan blue was determined, and the survival rate was calculated according to the following equation. The result is shown in FIG. 4.

$$\text{Survival rate (\%)} = \frac{\text{Number of living cells after application of electric pulse}}{\text{Number of seeded cells}} \times 100 \quad \text{(Equation 1)}$$

As shown in FIG. 3, when electric pulse was not applied, EGFP was not expressed at all. On the contrary, transfection was observed in cells electrically pulsed. The transfection efficiency was calculated by the following equation using the number of the adhering cells, determined from the image of a bright field microscope and the number of cells expressing fluorescent protein determined from the image of a fluorescence microscope.

$$\text{Transfection efficiency (\%)} = \frac{\text{Number of cells expressing fluorescent protein}}{\text{Number of whole cells adhering to the electrode}} \times 100 \quad \text{(Equation 2)}$$

The transfection efficiency was highest at the field strength of 75 V/cm. When an electric pulse was applied at 200 V/cm or more, the transfection efficiency was remarkably lowered. Further, as shown in FIG. 4, with respect to the cell survival rate after the application of an electric pulse, assessed by the trypan blue dye exclusion method, the cell survival rate was high at the field strength of 100 V/cm or less. At 150 V/cm or more, many cells were detached and died upon application of an electric pulse. It was also observed that the cells remaining on the electrode were remarkably damaged. The result that no transfection was observed without pulsing suggests that DNA is released from the surface of the electrode by electric pulsing and that the released DNA is introduced into cells through the cell membrane destabilized by electric pulsing or micropores formed in the cell membrane by pulsing.

EXAMPLE 3

In a similar manner to Example 1, HEK293 cells were seeded and adhered to the DNA-loaded gold electrode. Then, an electric pulse (field strength of 75 V/cm, pulse duration of 10 msec and the pulse number of 1) was applied to carry out electroporation. In the preparation of DNA-loaded electrode, the cationic polymers with different molecular weights were loaded to study the effect of the molecular weight of cationic polymers on the transfection efficiency. As cationic polymers, polyethyleneimines of the molecular weight of 800, 25000 and 750000 (referred to as PEI 800, PEI 25000 and PEI 750000; all of them are manufactured by Aldrich Co.) and polyallylamine hydrochlorides of the molecular weight of 15000 and 70000 (referred to as PAA 15000 and PAA 70000; all of them are manufactured by Aldrich Co.) were used.

Figure 5:
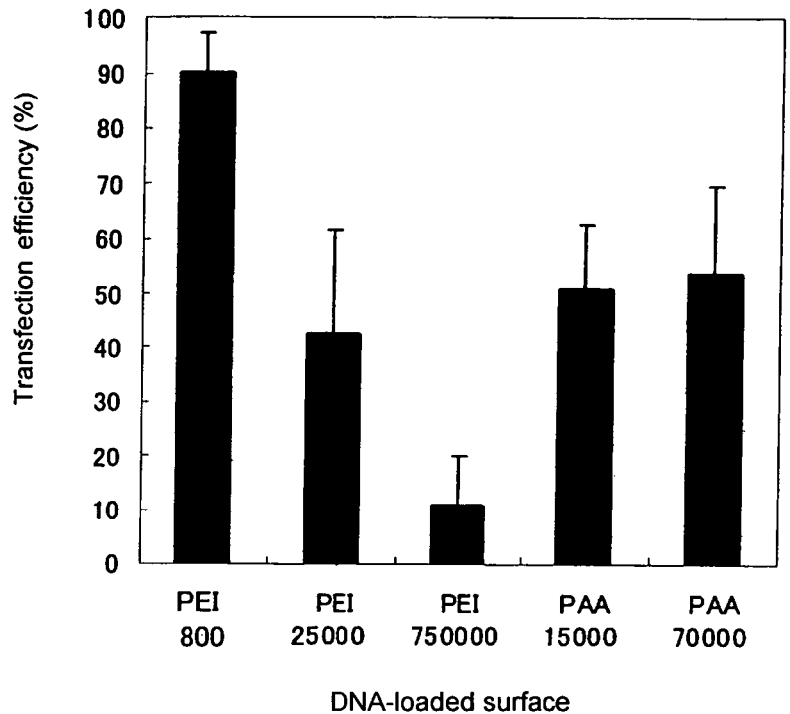
FIG. 5 is a diagram showing the effect of molecular weight of polyethyleneimine and polyallylamine on the transfection efficiency.
Figure 6:
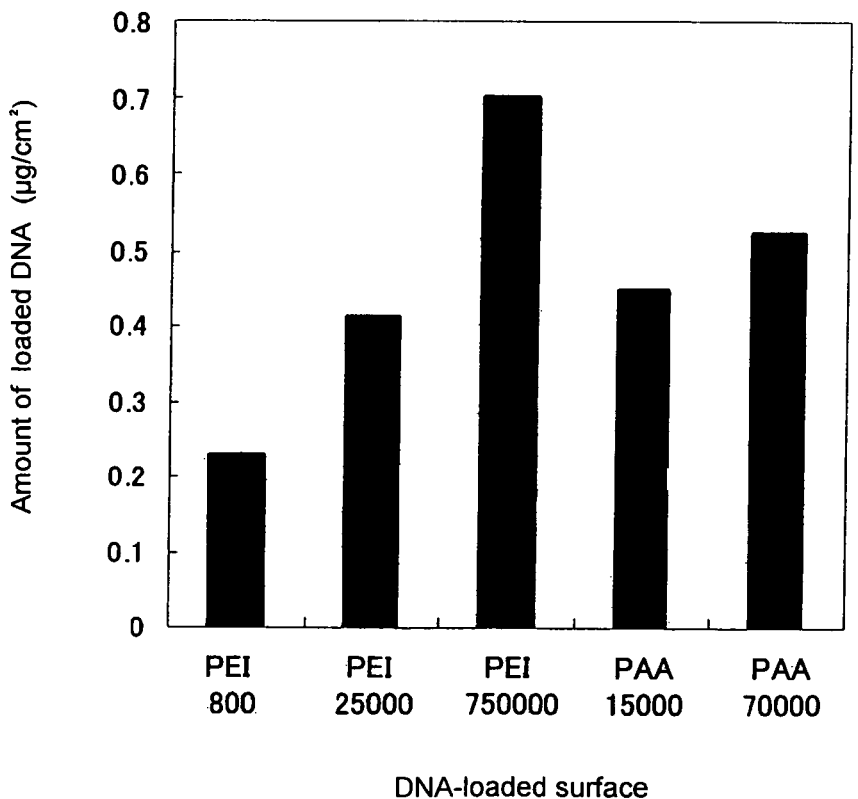
FIG. 6 is a diagram showing the amount of DNA loaded to the electrode with various cationic polymers.
Figure 7:
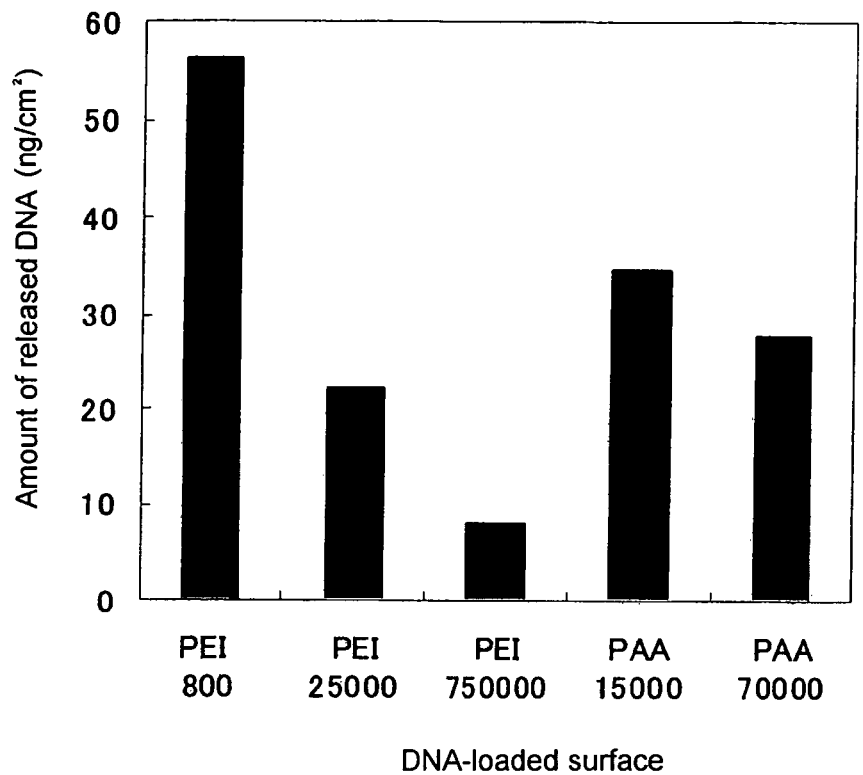
FIG. 7 is a diagram showing the amount of DNA released upon electric pulsing from the electrode surface with various cationic polymers.

FIG. 5 shows the relationship between the transfection efficiency and the molecular weights of polyethyleneimine and polyallylamine. As can be seen from the figure, the transfection efficiency was lowered with an increase in the molecular weight of polyethyleneimine. FIG. 6 shows the amount of DNA loaded on these surfaces. Further, after an electric pulse (field strength of 75 V/cm, pulse duration of 10 msec and the pulse number of 1) was applied, the amount of DNA released from the surface was evaluated by measuring the amount of DNA contained in the supernatant liquid by PicoGreen. The results are shown in FIG. 7. As apparent from these figures, the amount of loaded DNA was increased as the cationic polymers become to have a higher molecular weight, but the amount of DNA released from the surface after application of an electric pulse was rather smaller with cationic polymers with higher molecular weights than those with lower molecular weights. Although the amount of loaded DNA is small on the surface prepared with a low molecular weight polyethyleneimine (PE1800), about 30% of loaded DNA was released upon application of an electric pulse.

Figure 8:
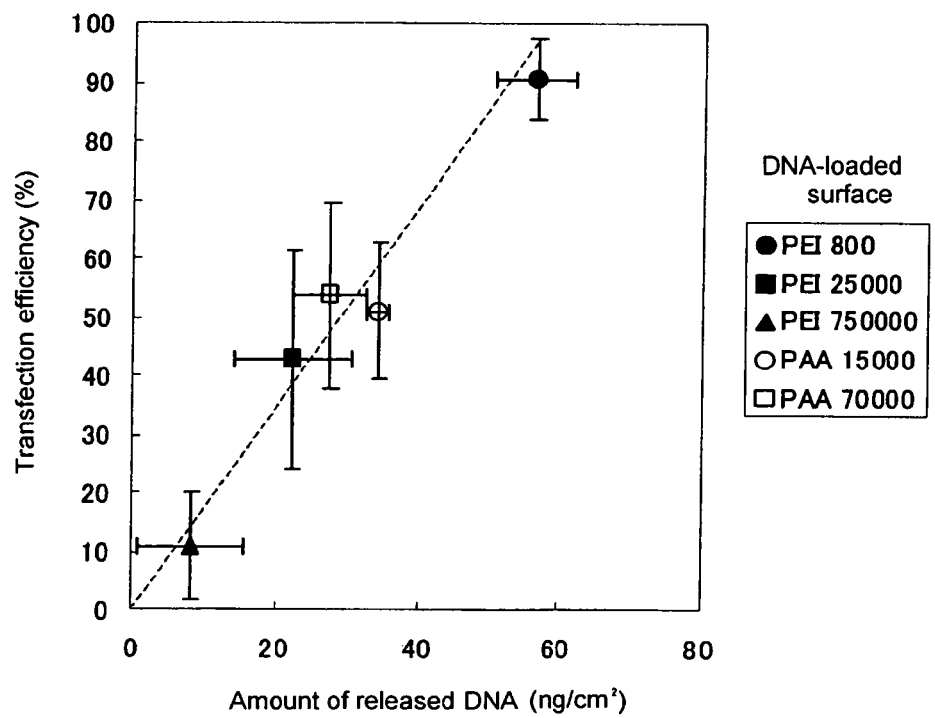
FIG. 8 shows the correlation between the efficiency of transfection and the amount of released DNA.

FIG. 8 shows the relationship between the transfection efficiency on the surfaces prepared with various cationic polymers and the amount of DNA released upon pulse application. As apparent from the figure, positive correlation is observed between the transfection efficiency and the amount of DNA released. As a result, it is suggested in the present invention that the transfection efficiency depends intensely on the amount of DNA released from the electrode surface.

EXAMPLE 4

In a similar manner to Example 1, HEK293 cells were seeded and adhered to the DNA-loaded gold electrode substrate and then electric pulse was applied to the cells to carry out electroporation. In this experiment, culture periods before the application of an electric pulse was changed to study the effect of the culture period on the transfection efficiency.

Figure 9:
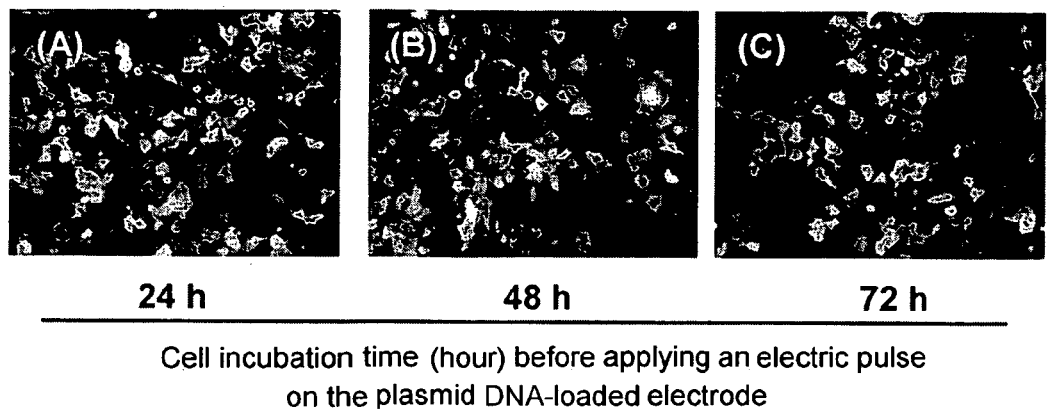
FIG. 9 shows fluorescence images of HEK293 cells 48 hr after electric pulsing. An electric pulse was applied (A) 24, (B) 48, and (C) 72 hr after cell seeding to the DNA-loaded electrode.
Figure 10:
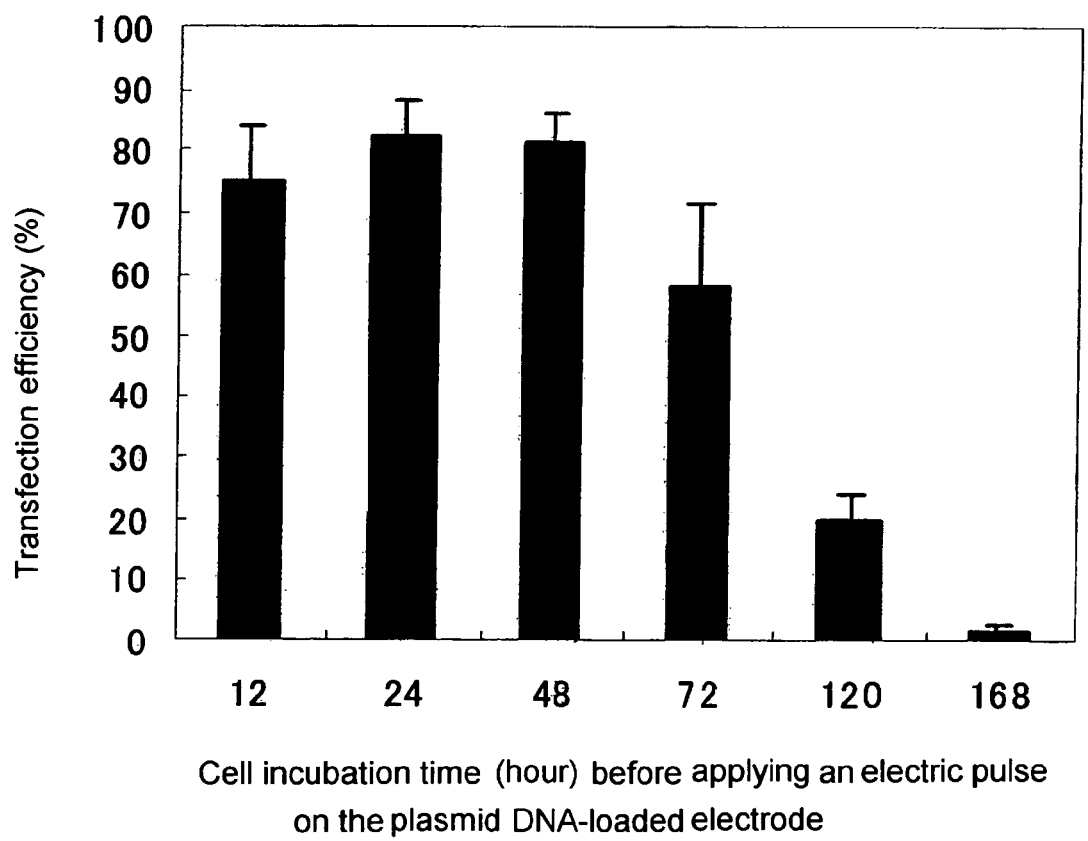
FIG. 10 is a diagram showing the transfection efficiency when cell incubation period until applying electric pulse is changed.

FIG. 9 shows the phase contrast microphotograph of cells 48 hours after the application of an electric pulse that was applied at 24, 48 or 72 hours after cell seeding. It is seen from the figure that the gene is efficiently expressed in the cells cultured for 24, 48 and 72 hours before electric pulsing. Further, FIG. 10 shows the relationship between the culture period before electric pulsing and the transfection efficiency (%). It is revealed from the results that the efficient transfection is achieved for any case where cells were cultured for 12, 24, 48 and 72 hours before electric pulsing, so that the introduction of the genes into the adhering cells can be accomplished at desirable timing.

EXAMPLE 5

(Experimental Proof for Primary Cells)

Hippocampus was collected from rat embryonic brain to obtain nerve cells. The introduction of a plasmid DNA encoding EGFP or red fluorescent protein (DsRed) was carried out for the primary nerve cells in a similar fashion to Example 1.

Namely, in a similar manner to Example 1, plasmid DNAs (pEGFP and pDsRed, manufactured by Clontech Laboratories Inc.) which encode green fluorescent protein (EGFP) and red fluorescent protein (DsRed) were loaded to the cationic surface of a gold electrode (cationic polymer: PEI800), the primary nerve cells were cultured on the surface for 3 days, and an electric pulse (125 V/cm, 10 msec and a single pulse) was applied. The analysis of transient expression of the introduced genes was analyzed 48 hours after the application of an electric pulse.

(Result)

Figure 11:
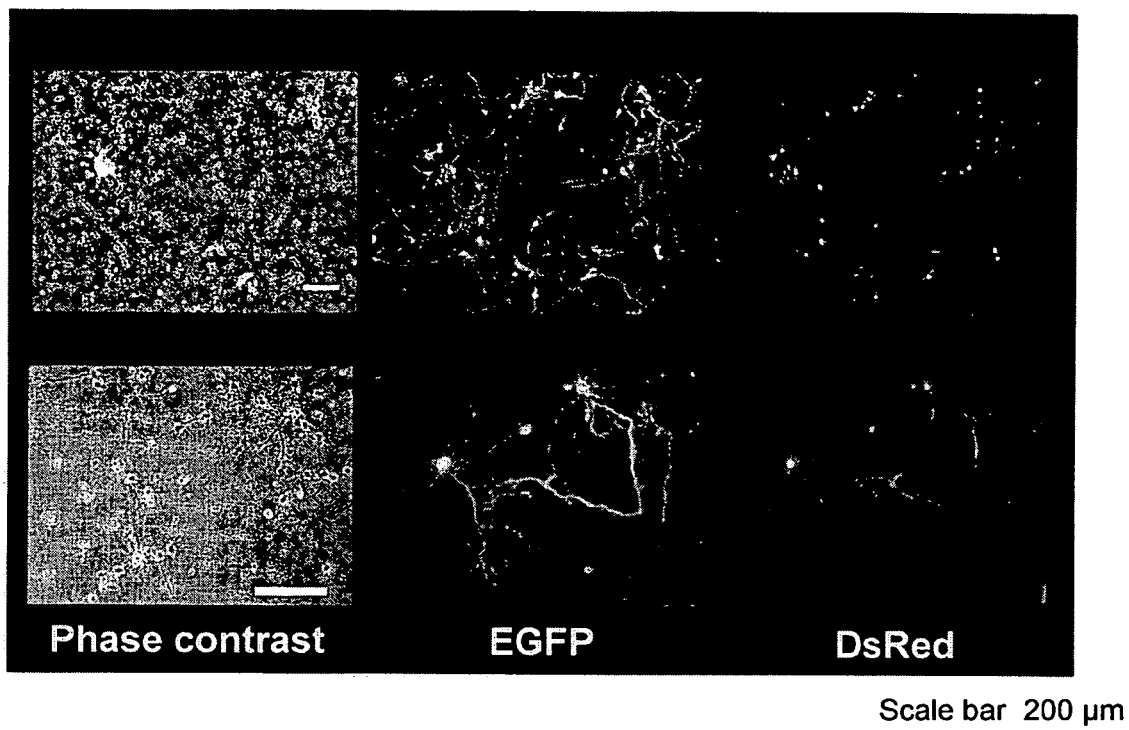
FIG. 11 shows (left) phase contrast and (middle, right) fluorescence microscopic images of primary hippocampal neurons 48 hours after electric pulsing on the surface loaded with a mixture of pEGFP and pDsRed. Photographs at an upper stage and a lower stage show images at different sights where electroporation was carried out under the same condition.

FIG. 11 shows phase contrast (left: phase contrast) and fluorescence microphotographs (middle: EGFP, right: DsRed) of hippocampal neurons 48 hours after electric pulsing. It is seen from the phase contrast images that cell damages are not noticeable after electroporation. Further, it can be seen from the middle (EGFP) and right (DsRed) microphotographs that both pEGFP and pDsRed are introduced into the cells, and that fluorescent proteins, EGFP and DsRed, encoded by these plasmids are expressed. These results demonstrate that multiple genes can be efficiently introduced into primary cultured cells by the present method.

The transfection efficiency was 20% for hippocamal neurons, when determined in a similar manner as in the case with HEK293 cells. When pEGFP and pDsRed were introduced in the primary nerve cells by a conventional lipofection method (refer to Comparative Example 1 mentioned below) and electroporation method (refer to Reference Example 2 mentioned below) for comparison, the transfection efficiency was 10 to 20% and no significant differences were observed between these methods and the present invention. However, cell damages were observed to a great extent and many cells were died in the conventional methods. Percent dead cells reached 20 to 30%. On the other hand, cell damages were not observed at all by the gene introduction method of the present invention.

COMPARATIVE EXAMPLE 1

Hippocampus neurons collected were seeded in a 24 well plate coated with poly(L-lysine) to the 70 to 80% confluence, and gene introduction was performed using Lipofectamine 2000 (manufactured by Invitrogene Inc.). 1 μg of plasmide DNA and 2 μl of Lipofectamine 2000 were used. Lipofection 2000 and DNA were separately diluted with 50 μl of Opti- MEM (serum-free culture medium). These solutions were mixed and kept at room temperature for 20 min, and the solution was added to the cells to carry out lipofection. An expression of EGFP was analyzed by a fluorescence microscope 48 hours after the lipofection. As described above, the transfection efficiency was 10 to 20%.

COMPARATIVE EXAMPLE 2

Hippocampus neurons were rinsed with PBS and suspended in PBS to the concentration of $1 \times 10^6$ cells/ml. To the suspension (200 μl), 15 μg of plasmid DNA (pEGFP) was added, followed by mixing. The suspension was injected into an electroporation cuvet and kept on ice for 10 min. Then, electroporation was carried out under the conditions of the field strength of 625 V/cm (distance between electrodes: 4 mm), a pulse duration of 10 msec and the pulse number of 1. After pulsing, the suspension was kept in the cuvet at room temperature for 10 minutes and then, seeded to a 60 mm PLL-coated cell culture dish. Forty-eight hours after electroporation, the expression of EGFP was analyzed by a fluorescence microscope. As described above, the transfection efficiency was 10 to 20%.

EXAMPLE 6

Two plasmids (pEGFP or pDsRed) were separately loaded in a small area (5 mm in diameter) on the cationic surface of an electrode which was prepared in a similar manner to Example 1. In a similar manner to Example 1, HEK293 cells were adhered and grown on the DNA-loaded gold electrode, non-adhered cells were removed 24 hours after cell seeding, and then an electric pulse (75 V/cm, 10 msec and the pulse number of 1) was applied.

Figure 12:
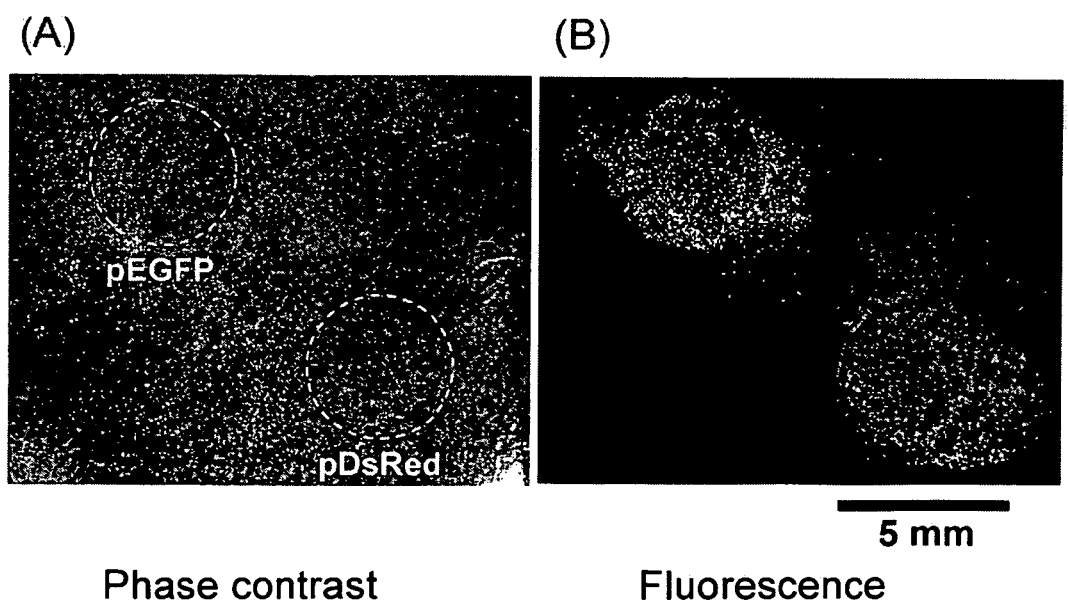
FIG. 12 shows (left) phase contrast and (right) fluorescence images of HEK293 cells 48 hours after electric pulsing on the surface loaded with pEGFP or pDsRed at the restricted site.

FIG. 12 shows (left) phase contrast and (right) fluorescence microphotographs of HEK293 cells 48 hours after electric pulsing. The images are acquired at low magnification in order to observe the large area on the electrode (about $1.5 \times 1.5$ cm$^2$). It is seen that cells uniformly adhered to the surface of the electrode. Further, fluorescence images were acquired for the areas where PEGFP and pDsRed were loaded. These images were merged and shown in the right figure. As can be seen, fluorescence from EGFP and DsRed is observed at the loading areas of the respective genes. This result indicates that the method of the present invention allows to introduce at the restricted sites.

EXAMPLE 7

A glass substrate on which indium-tin oxide (hereinafter, referred to as ITO) was deposited on one side was treated with oxygen plasma (output power of 30 W and pressure of 5 Pa) at room temperature for 5 minutes using a plasma generator (Model: PA300AT manufactured by Okuma Engineering Co.) to remove impurities from the surface.

Then, a phosphate buffered saline (pH=7.4) containing polyethyleneimine having an average molecular weight of 800 (hereinafter, referred to as PEI800, manufactured by Aldrich Co., Ltd.) at a concentration of 1% was added on the surface of ITO and kept at room temperature for 30 minutes. The surface of the ITO was adequately rinsed with water and dried under nitrogen gas to obtain ITO with a cationic surface. Then, a silicone frame (inner area: $1.3 \times 1.3$ cm$^2$ and height: 1 mm) sterilized with ethanol was fixed to the cationic surface of the ITO electrode obtained above. Then, the phosphate buffered saline (pH=7.4) containing 0.05 mg/ml plasmid DNA encoding green fluorescent protein (pEGFP-Cl, manufactured by Clontech Laboratories Inc.) was added to the cationic surface of the ITO electrode within the silicone frame, and kept at room temperature for 30 minutes to electrostatically adsorb DNA onto the ITO surface. Then, the surface was adequately rinsed with phosphate buffered saline in order to remove DNA which was not adsorbed. Thereafter, PEI800 and DNA were adsorbed alternately in a similar manner, and then the surface was adequately rinsed with phosphate buffered saline to obtain a DNA-loaded transparent electrode substrate.

Hereinafter, the number of alternate adsorption cycles for an untreated ITO electrode is referred to as zero, and each step for adsorbing PEI and DNA is counted as one cycle. Namely, the alternate adsorption cycles was expressed as 3 for the surface with PEI800-DNA-PEI800. The atomic composition of the ITO surface on which PEI800 and DNA were alternately adsorbed was determined with X-ray photoelectron spectroscopy (XPS). The results are shown in Table 1.

TABLE 1

| | (Unit: percent) | | | | | |
| --- | --- | --- | --- | --- | --- | --- |
| Cycle number | C | N | O | P | In | Sn |
| 0 | 8.9 | 0 | 70.5 | 0 | 17.9 | 2.7 |
| 1 | 19.7 | 9.3 | 55.5 | 0 | 13.5 | 2.1 |
| 2 | 35.4 | 15.9 | 38.2 | 3.5 | 5.9 | 1.1 |
| 3 | 43.3 | 18.2 | 30.1 | 3.2 | 4.5 | 0.77 |
| 4 | 48.3 | 16.8 | 27.8 | 4.7 | 1.9 | 0.45 |
| 5 | 52.2 | 22.3 | 20.9 | 3.7 | 0.75 | 0.19 |
| 6 | 48.3 | 20.7 | 26.7 | 3.8 | 0.49 | 0.06 |
| 7 | 55.8 | 22 | 18.7 | 3.5 | 0.01 | 0 |

As can be seen in Table 1, N was detected on the surfaces with adsorbed PEI800, and P was detected on the surfaces with adsorbed DNA. Further, the atomic composition of In and Sn contained in ITO decreased with an increase in the cycle number. These results indicate that PEI800 and DNA exist on the surface of the ITO electrode and that the thickness of an adsorbed layer increased with the cycle number.

Figure 13:
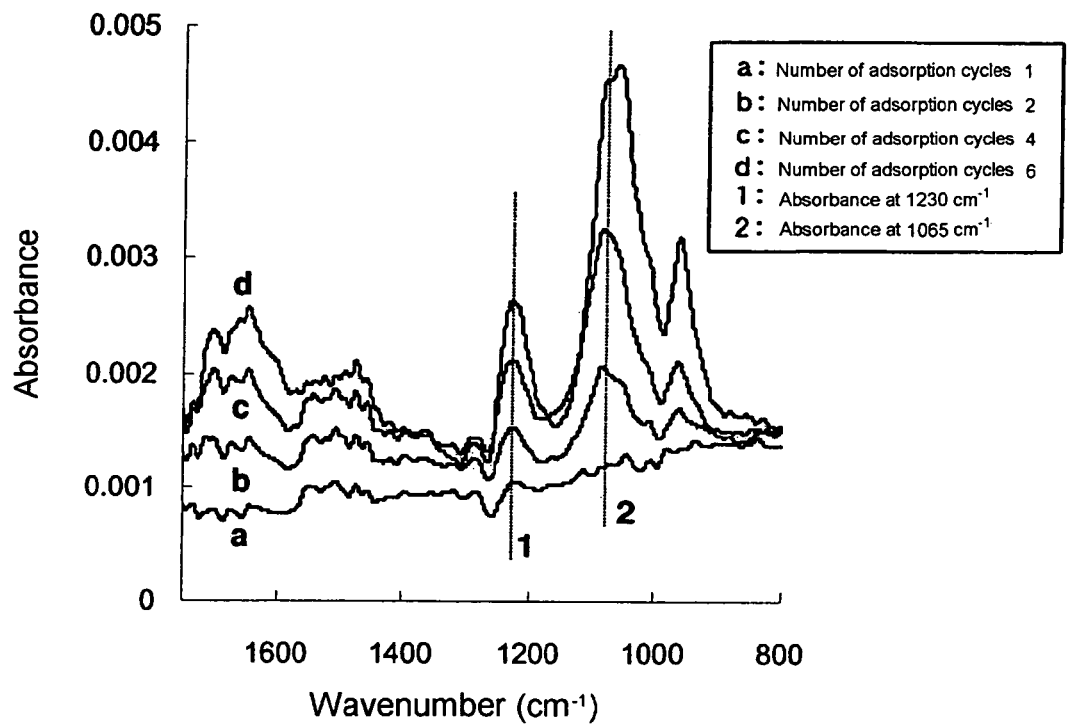
FIG. 13 shows ATR-infrared absorption spectra for ITO surfaces obtained after different numbers of alternate adsorption cycles.
Figure 14:
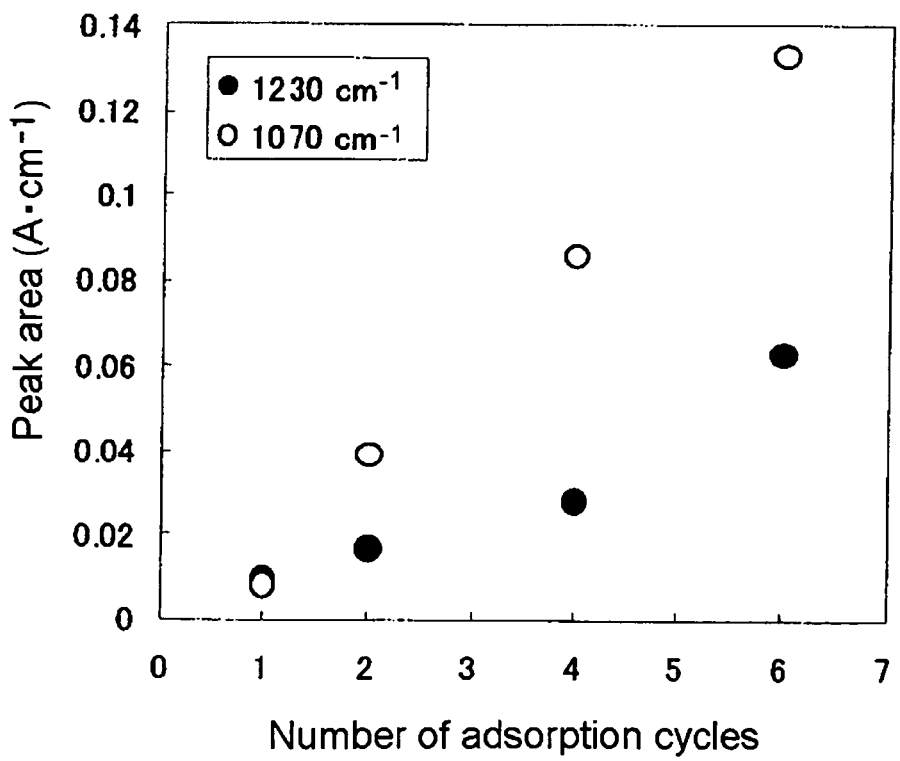
FIG. 14 shows the relationship between the number of alternate adsorption cycles and the peak areas for 2 absorption bands assigned for phosphate group.

FIG. 13 shows ATR-IR spectra recorded for the surface of the ITO electrode on which PEI800 and DNA were alternately adsorbed. Two absorption bands at 1065 and 1230 cm$^{-1}$ are assigned for a phosphate group in the DNA backbone. As can be seen from FIG. 13, when the number of adsorption cycles increased, these absorptions increased. In FIG. 14, peak areas for these two absorption bands are plotted against the number of adsorption cycles. The peak areas were linearly increased with an increase in the cycle number. This result suggests that the amount of DNA loaded to the ITO surface increases with an increase in the number of adsorption cycles.

Figure 15:
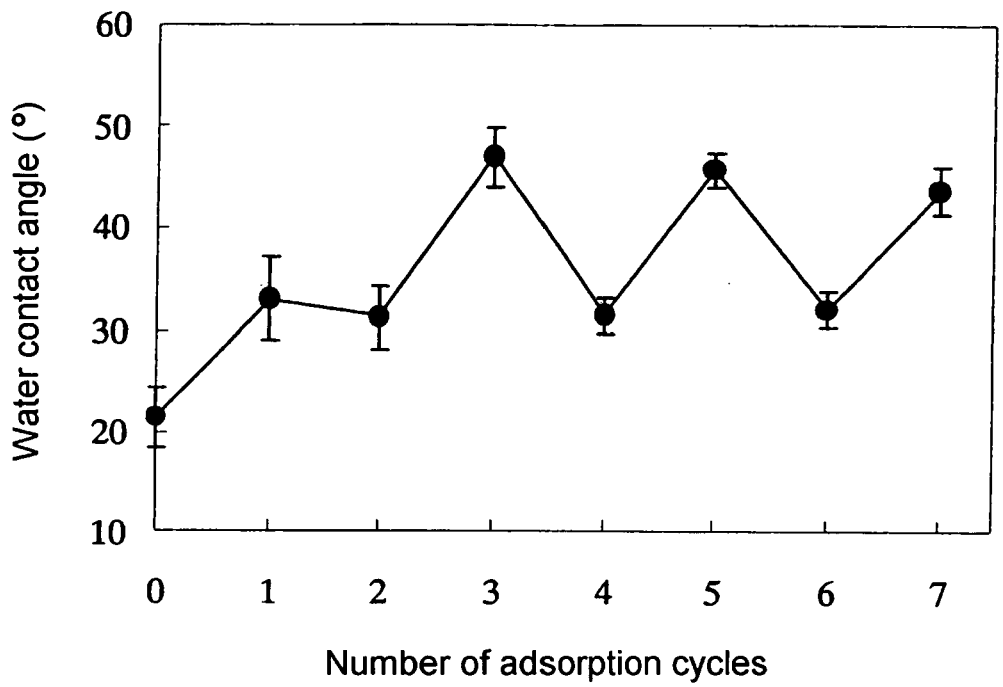
FIG. 15 shows the relationship between the number of alternate adsorption cycles and the water contact angle of the ITO surface.

Then, the water contact angle was measured on the ITO surface onto which PEI800 and DNA were alternately adsorbed to study the change of the wettability of the surfaces. The results are shown in FIG. 15. When PEI800 was present at the outermost surface, water contact angle was approximately 45 degree, while in the case of DNA, water contact angle was about 32 degree. As can be seen from FIG. 15, the contact angle was changed alternately in accordance with the type of the outermost surface. This result suggests that the alternate adsorption layers made of PEI800 and DNA are formed on the surface of the ITO electrode. Contact angle on the surface where one layer of PEI800 was adsorbed is lower than that on the PEI800-adsorbed surfaces thereafter. It is likely that the first layer of PEI800 does not perfectly cover the ITO surface and that the basement ITO surface of a base material is partially exposed.

EXAMPLE 8

Electroporation of cells was carried out on the DNA-loaded ITO electrode which was prepared according to Example 7. Firstly, human embryonic kidney cells (HEK293: obtained from Human Science Foundation) were suspended in a serum containing culture medium (composition of culture medium: minimum essential culture medium (MEM) (Gibco Life Technology), 10% fetal bovine serum, 100 units/ml penicillin, 0.1 mg/ml streptomycin), and the suspension was added to the surface of the DNA-loaded transparent electrode (lamination number=5 and base material: poly(ethylene terephthalate) (PET)). The cells were cultured at 37° C. under 5% $CO_2$ atmosphere to adhere to the electrode. After 24 hours, the culture medium was exchanged with phosphate buffered saline (pH=7.4) at 4° C. to remove cells which were not adhered. The well of the silicon frame was filled with the phosphate buffered saline and then, the glass plate on which a gold thin film was deposited on one side was placed on the silicone frame as the second electrode. Their arrangement is shown in FIG. 1 (provided that the symbol E is an ITO electrode in the present Example).

Then, the DNA-loaded ITO electrode was set as cathode (−) and the upper gold electrode was set as anode (+). They were connected to a high voltage pulse generator (Electrosquarereportor T820, manufactured by BTX Inc.) and an electric pulse was applied at the field strength of 250 V/cm, a pulse duration of 10 msec and a pulse number of 1, thereby to carry out electroporation. After application of a pulse, the cells were incubated at room temperature for 5 min. Then the phosphate buffered saline in the wells was exchanged with a serum-containing culture medium which was previously kept at 37° C., and the cells were incubated at 37° C. under atmosphere of 5% $CO_2$.

The transient expression of the introduced gene was analyzed 48 hours after electroporation. The cells emitting green fluorescence due to expression of green fluorescent protein (EGFP) were counted under a fluorescence microscope, and transfection efficiency was determined as the number of EGFP positive cells per total number of cells.

Figure 16:
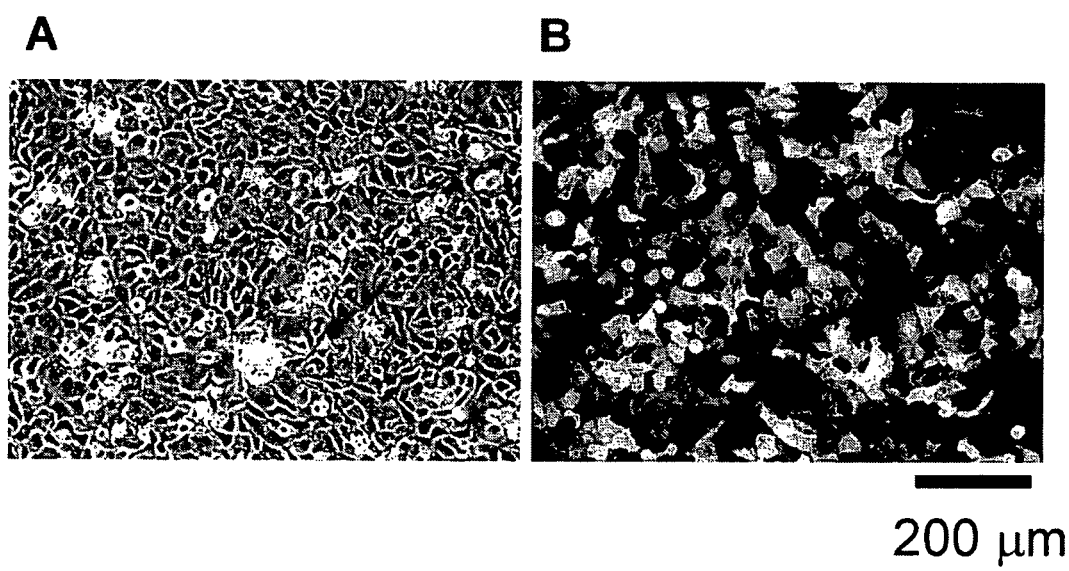
FIG. 16 shows (A) phase contrast and (B) fluorescence microscopic images of HEK293 cells 48 hours after electric pulsing on the DNA-loaded ITO surface (a field strength of 250 V/cm, a pulse duration of 10 msec and a pulse number of 1).

FIG. 16 shows (A) phase contrast and (B) fluorescence microphotographs of HEK293 cells 48 hours after electroporation. As can be seen from the figure, approximately 70% of total cells expressed EGFP. This result clearly demonstrates that the procedure of the present invention permits efficient introduction of genes. Further, a bright image with high resolution obtained in the observation of cells using fluorescence and phase contrast microscopes (when glass was used as a base material). This emphasizes that the observation of cells can be favorably carried out by using a transparent electrode.

EXAMPLE 9

In a similar manner to Example 8, HEK293 cells were seeded on the DNA-loaded transparent electrode to adhere, and then an electric pulse was applied to carry out electroporation. The voltage of an electric pulse was changed to study the effect of the field strength on the transfection efficiency. The conditions of pulse application other than voltage were the same as in Example 8 (a pulse duration of 10 msec and a pulse number of 1). Transfection efficiency was evaluated as the percentage of EGFP positive cells 48 hours after the application of an electric pulse. Further, the effect of the field strength for cell survival rate was simultaneously studied. The cell survival rate was evaluated by the trypan blue dye exclusion method for the cells harvested by trypsin treatment 48 hours after the application of an electric pulse. Namely, the number of living cells that were not stained with trypan blue was determined and a proportion to the number of living cells (control) to which an electric pulse was not applied was calculated. The cell survival rate was calculated using the following equation.

$$\text{Cell survival rate (\%)} = \frac{\text{Number of living cells 48 hours after electric pulsing}}{\text{Number of living cells after incubation for 48 hours without pulse application}} \times 100 \quad \text{(Equation 3)}$$

Figure 17:
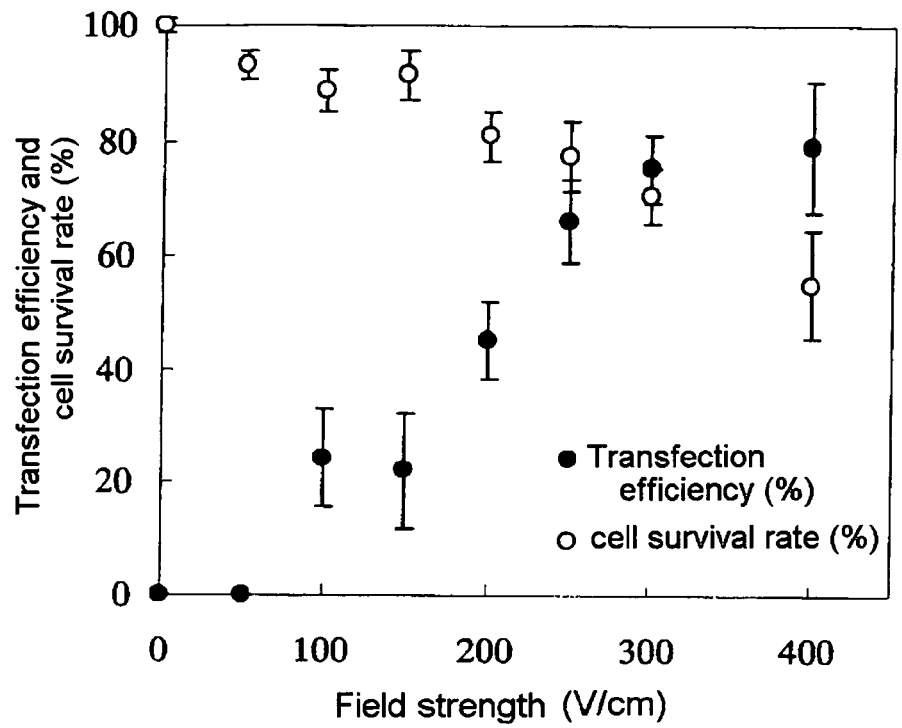
FIG. 17 is a diagram showing the effect of field strength on transfection efficiency and cell survival rate on the DNA-loaded ITO surface.

The result is shown in FIG. 17. As shown in FIG. 17, no EGFP was expressed when a pulse was not applied. On the other hand, EGFP was expressed in the cells that were electrically pulsed. The transfection efficiency was calculated by the following equation using the number of the total living cells on the electrode, determined by the trypan blue dye exclusion method, and the number of fluorescent protein-expressing cells, determined from fluorescence images.

$$\text{Transfection efficiency (\%)} = \frac{\text{Number of cells expressing fluorescent protein}}{\text{Number of total living cells}} \times 100 \quad \text{(Equation 4)}$$

The transfection efficiency was increased linearly with an increase in the field strength. When an electric pulse was applied at 300 V/cm or more, the transfection efficiency reached a plateau level (approx. 80%). On the other hand, the cell survival rate after the application of an electric pulse remained high at the field strength of 250 V/cm or less. At 300 V/cm or more, many cells were detached and died upon application of an electric pulse. The result that no transfection was observed without pulsing suggests the mechanisms that the release of DNA from the electrode surface upon electric pulsing and the destabilization of a cell membrane to generate micropores, takes place simultaneously to enhance introduction of the DNA into the cells.

EXAMPLE 10

In a similar manner to Example 8, HEK293 cells were seeded on the DNA-loaded ITO electrode (the number of adsorption cycles=5 and base material: PET) to adhere and then an electric pulse (a field strength of 250 V/cm, a pulse duration of 10 msec and a pulse number of 1) was applied to carry out electroporation. In this example, the number of adsorption cycles for PEI800 and DNA was changed to study the effect of the cycle number on transfection efficiency.

Figure 18:
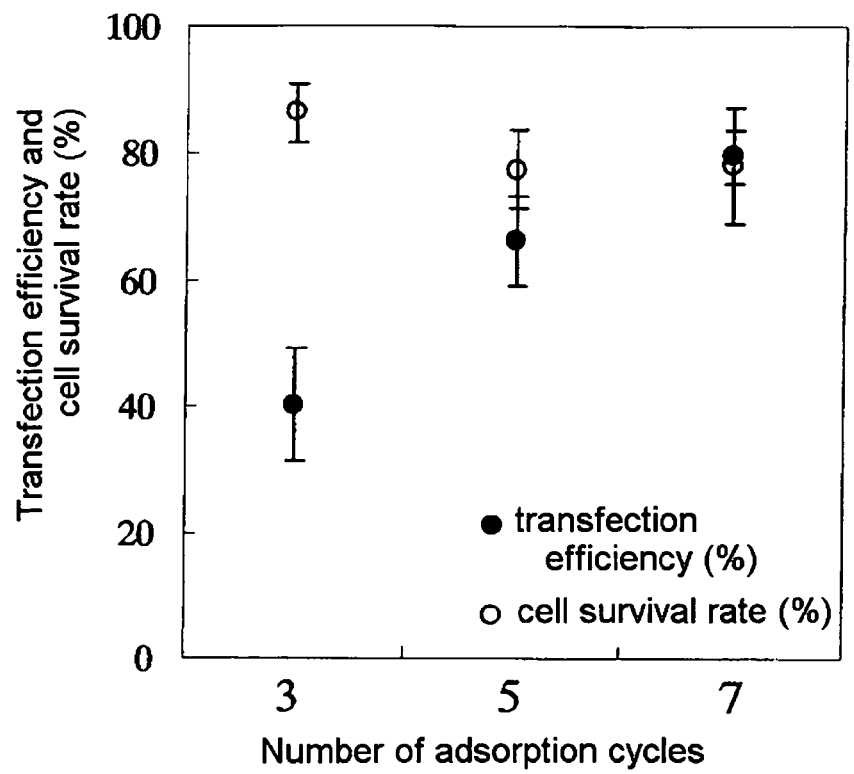
FIG. 18 is a diagram showing the effect of the number of alternate adsorption cycles on transfection efficiency and cell survival rate on the DNA-loaded ITO surface.
Figure 19:
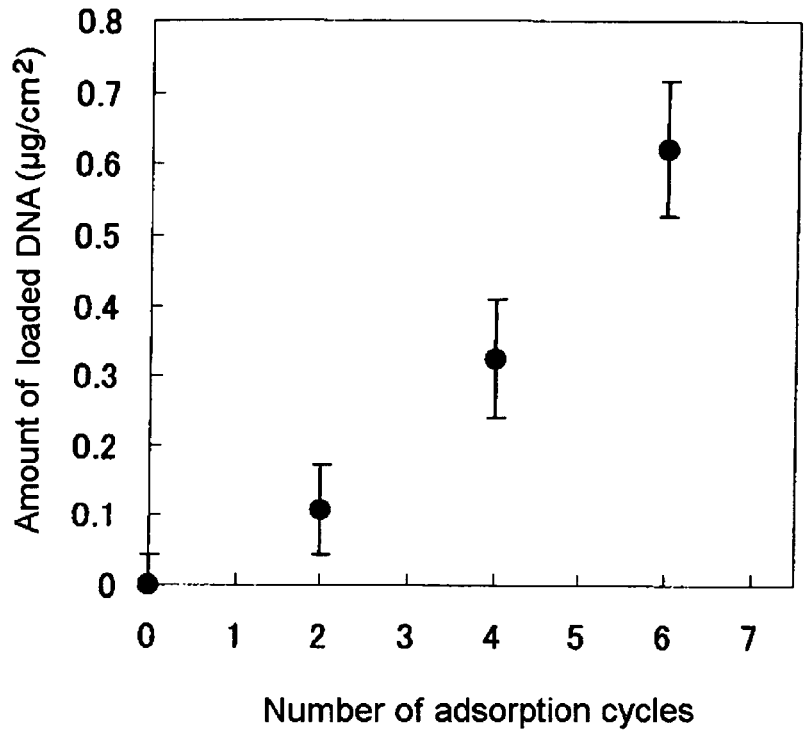
FIG. 19 is a diagram showing the amount of DNA loaded to the ITO surface after different numbers of alternate adsorption cycles.

FIG. 18 shows the relationship between the transfection efficiency and the cycle number. As can be seen from the figure, the larger number of adsorption cycles gave rise to more efficient transfection while keeping cell survival rate. FIG. 19 shows the amount of DNA-loaded to the surface after different members of adsorption cycles. It is seen that the amount of loaded DNA increased with an increase in the number of adsorption cycles.

Figure 20:
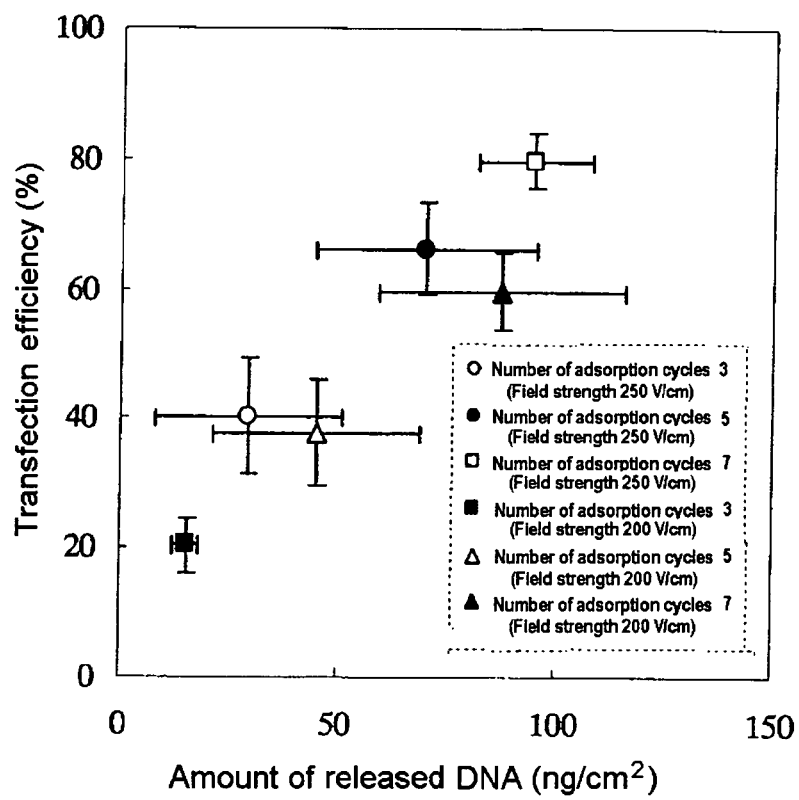
FIG. 20 is a correlation chart showing the relationship between transfection efficiency and the amount of released DNA.

After an electric pulse (field strength of 200 to 300 V/cm, a pulse duration of 10 msec and a pulse number of 1) was applied, the amount of DNA released from the surface was evaluated by measuring the amount of DNA contained in supernatant using PicoGreen (manufactured by Molecular Probe Inc.) which is a fluorescent dye. FIG. 20 shows the relationship between the transfection efficiency determined for various samples and the amount of DNA released from these surfaces upon pulsing. As can be seen, the amount of released DNA increased with an increase in the number of adsorption cycles. Approximately 10 to 30% of loaded DNA was released by application of an electric pulse. As apparent from the figure, the transfection efficiency correlates positively to the amount of DNA released. Therefore, it is suggested that the transfection efficiency in the present invention is primarily governed by the amount of DNA released from the surface.

EXAMPLE 11

(Experimental Proof for Primary Cell)

Hippocampus neurons were prepared from the rat embryonic brain. The electroporation of cells with plasmid DNA encoding EGFP or red fluorescent protein (DsRed) was carried out for the primary neurons by the similar method as in Example 8.

Namely, in a similar manner to Example 8, plasmid DNAs (pEGFP and pDsRed, manufactured by Clontech Laboratories Inc.) which encode green fluorescent protein (EGFP) and red fluorescent protein (DsRed) were loaded to the surface of a transparent ITO electrode (the number of adsorption cycles=5, electrode: ITO, base material: glass), primary neurons were cultured on the surface for 3 days and then an electric pulse (200 V/cm, 10 msec and 1 cycle) was applied. The transient expression of EGFP and DsRed was analyzed 48 hours after electric pulsing.

(Result)

Figure 21:
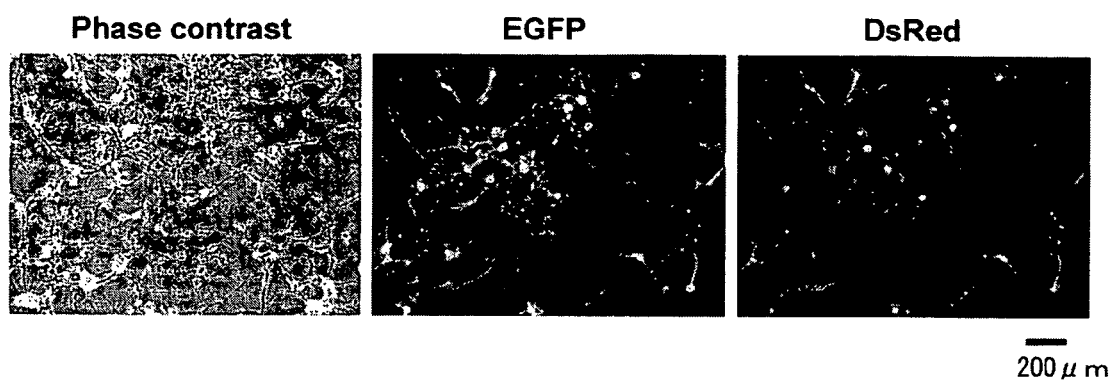
FIG. 21 shows (left) phase contrast and (middle, right) fluorescence microscopic images of hippocampal neurons 48 hours after electric pulsing on the ITO surface loaded with a mixture of pEGFP and pDsRed. Photographs at an upper stage and a lower stage show images at different sights where electroporation was carried out under the same condition.

FIG. 21 shows phase contrast (left, phase contrast) and fluorescence (middle, right, EGFP, DsRed) microphotographs 48 hours after electric pulsing. No damages were observed in the pulsed cells, when assessed from the left microscopic images. Fluoresce images (middle and right images in FIG. 21) show that both pEGFP and pDsRed are introduced into the cells, and fluorescent proteins EGFP and DsRed which are expressed in the cells. Furthermore, the figure demonstrates that different genes can be efficiently introduced by the present method. This result also indicates that electroporation could successfully be carried out even after 3-day incubation of the cells before pulsing, showing that the present method can be used for transfection at a preferable moment after cell seeding.

EXAMPLE 12

(Arraying of Nucleic Acids on the Surface of ITO Electrode, and Electroporation on the Array)

The surface of ITO electrode (base material: glass) was cleaned by the treatment with oxygen plasma. Then, the ITO electrode was immersed in a 1% toluene solution of octadecyltriethoxysilane (LS-6970, Shin-Etsu Chemical Co., Ltd.) and left alone at room temperature for 2 hours. After adequately rinsed with toluene and ethanol, the electrode was heated at 80° C. for 12 hours. Then, a photo mask in which a chrome pattern was deposited on a glass substrate was placed on the surface of the electrode and ultraviolet light was irradiated through the pattern at room temperature for 1 hour. After the mask was removed, the substrate was rinsed with ethanol to remove a decomposed organic silane layer due to ultraviolet irradiation. As a result, a patterned surface comprising a region of a hydrophobic organosilane monolayer and islands on which hydrophilic ITO surface was exposed was obtained.

PEI800 and plasmid DNA (pEGFP, pDsRed or a mixture of both) were alternately adsorbed (number of adsorption cycles=5) by manually pipetting these solutions to the different ITO spots on the patterned ITO electrode (circular spot where ITO was exposed: a diameter of 1 mm, 10×10 spots). In a similar manner to Example 8, HEK293 cells were adhered to the DNA-loaded array, and an electric pulse (200 V/cm, 10 msec and 1 pulse) was applied 24 hours after cell seeding, after non-adhered cells were removed.

Figure 22:
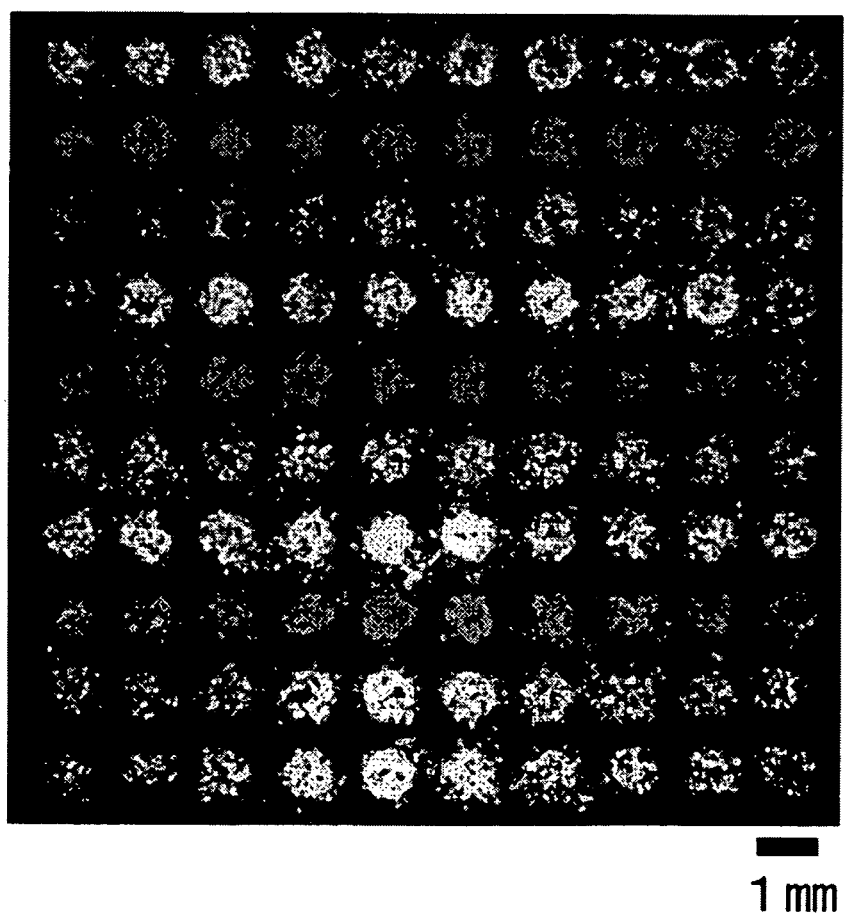
FIG. 22 is a fluorescence microscopic image of HEK293 cells 48 hours after electric pulsing on the ITO surface onto which different plasmids (PEGFP or pDsRed, or a mixture of both) were adsorbed in an array format.

FIG. 22 shows a fluorescence microphotograph 48 hours after electric pulsing. The image was acquired at low magnification to observe the whole area on the array (about 1.7×1.7 $cm^2$). Fluorescence images separately recorded for EGFP and DsRed were merged and are shown in FIG. 22. Fluorescence is observed on the spots where respective plasmids were loaded. Further, cells on the spots where both genes were mixed co-expressed both proteins. These results demonstrate that the present invention can provide a method for restricting the regions for transfection.

INDUSTRIAL APPLICABILITY

The method invented here can be used for efficiently introducing genes into cells without cell damage. The method further enables us to transfect cells at timing and at restricted sites. Consequently, the method of introducing nucleic acids according to the present invention serves for the functional analysis of genes and gene products at a cellular level, promoting the advances in cell biology, post genomic and proteome research, and consequently in medical care.

The invention claimed is:

1. A method of introducing a nucleic acid into cells by electroporation, comprising
    the step (a) of providing an electrode with a cationic surface;
    the step (b) of adsorbing and loading a nucleic acid onto the cationic surface of an electrode;
    the step (c) of allowing cells to adhere onto the surface of the nucleic acid-loaded electrode obtained in the step (b); and
    the step (d) of applying electric pulses to the cells, wherein the electrode with a cationic surface is an electrode on which a monolayer of a thiol, disulfide or sulfide compound having an anionic functional group at the terminal is formed and a cationic polymer is adsorbed onto the surface of the monolayer.

2. A method of introducing a nucleic acid into cells by electroporation, comprising
the step (a) of providing an electrode with a cationic surface;
the step (b) of adsorbing and loading a nucleic acid onto the cationic surface of an electrode;
the step (c) of allowing cells to adhere onto the surface of the nucleic acid-loaded electrode obtained in the step (b); and
the step (d) of applying electric pulses to the cells, wherein the electrode with a cationic surface is an electrode on which a monolayer of a thiol, disulfide or sulfide compound having a cationic functional group at the terminal or a silanising agent having a cationic functional group at the terminal is formed, an anionic polymer is adsorbed onto the surface of the monolayer and a cationic polymer is further adsorbed onto its surface.

3. A method of introducing a nucleic acid into cells by electroporation, comprising
the step (a) of providing an electrode with a cationic surface;
the step (b) of adsorbing and loading a nucleic acid onto the cationic surface of an electrode;
the step (c) of allowing cells to adhere onto the surface of the nucleic acid-loaded electrode obtained in the step (b); and
the step (d) of applying electric pulses to the cells, wherein the electrode with a cationic surface is a transparent electrode on which a cationic polymer is adsorbed.

4. The method according to claim 3, wherein the transparent electrode is a glass or a transparent plastic substrate on which indium-tin oxide, indium oxide, aluminum-doped zinc oxide or antimony-doped tin oxide is deposited.

5. The method according to claim 3, wherein the transparent electrode is a glass substrate or a transparent plastic substrate on which indium-tin oxide is deposited.

6. The method according to claim 1, wherein the electrode with a cationic surface is an electrode on which the monolayer of a thiol compound having an anionic functional group at the terminal is formed and a cationic polymer is adsorbed onto the surface of the monolayer, and the thiol compound having an anionic functional group at its terminal is a thiol compound indicated by the formula (1):

$$R^1(CH_2)_n\text{—SH} \quad (1)$$

wherein $R^1$ represents an anionic functional group and n represents an integer of 1 to 40.

7. The method according to claim 6, wherein $R^1$ is a group selected from the group consisting of a carboxyl group, a phosphate group, a sulfo group and a phosphonic acid group.

8. The method according to claim 6, wherein the thiol compound represented by the formula (1) is a mercaptoalkanoic acid selected from 11-mercaptoundecanoic acid, 8-mercaptooctanoic acid and 15-mercaptohexadecanoic acid.

9. The method according to claim 1, wherein the cationic polymer is a polymer selected from a polyethyleneimine, polyallylamine, polyvinylamine, polyvinylpyridine, aminoacetalized poly(vinyl alcohol), acrylic or methacrylic polymer having primary to quaternary amine at the terminal of the side chain, acid-treated gelatin, protamine, polylysine, polyornithine, polyarginine, chitosan, DEAE-cellulose, DEAE-dextran and polyamidoamine dendrimer.

10. The method according to claim 2, wherein the electrode with a cationic surface is an electrode on which a monolayer of a thiol compound having a cationic functional group at the terminal is formed, an anionic polymer is adsorbed onto the surface of the monolayer and a cationic polymer is further adsorbed onto its surface, and the thiol compound having a cationic functional group at the terminal is a thiol compound represented by the formula (2):

$$R^2(CH_2)_n\text{—SH} \quad (2)$$

wherein $R^2$ represents a cationic functional group and n represents an integer of 1 to 40.

11. The method according to claim 10, wherein $R^2$ is an amino group.

12. A method of introducing a nucleic acid into cells by electroporation, comprising
the step (A) of adsorbing and loading a nucleic acid onto the surface of an electrode;
the step (B) of allowing cells to adhere onto the surface of the obtained nucleic acid-loaded electrode; and
the step (C) of applying electric pulses to the adhering cells, wherein the step (B) is carried out by incubating cells on the nucleic acid-loaded electrode.

13. A method of introducing a nucleic acid into cells by electroporation, comprising
the step (a) of providing an electrode with a cationic surface;
the step (b) of adsorbing and loading a nucleic acid onto the cationic surface of an electrode;
the step (c) of allowing cells to adhere onto the surface of the nucleic acid-loaded electrode obtained in the step (b); and
the step (d) of applying electric pulses to the cells, wherein the step (c) is carried out by incubating cells on the surface of the nucleic acid-loaded electrode.

14. A method of introducing a nucleic acid into cells by electroporation, comprising
the step (a) of providing an electrode with a cationic surface;
the step (b) of adsorbing and loading a nucleic acid onto the cationic surface of an electrode;
the step (c) of allowing cells to adhere onto the surface of the nucleic acid-loaded electrode obtained in the step (b); and
the step (d) of applying electric pulses to the cells, wherein an electrode with the cationic surface is an electrode having a micropatterned surface.

15. An electrode with a cationic surface wherein a monolayer of a thiol, disulfide or sulfide compound having an anionic functional group at the terminal is formed and a cationic polymer is adsorbed onto the surface of the monolayer.

16. An electrode with a cationic surface wherein a monolayer of a thiol compound represented by the formula (1):

$$R^1(CH_2)_n\text{—SH}, \quad (1)$$

wherein $R^1$ represents an anionic functional group and n represents an integer of 1 to 40, is formed on the surface of a gold electrode substrate prepared by depositing gold onto a glass substrate and a cationic polymer is adsorbed onto the surface of the monolayer.

17. The method according to claim 13, wherein the electrode with a cationic surface is an electrode on which a monolayer of a thiol, disulfide or sulfide compound having an anionic functional group at the terminal is formed and a cationic polymer is adsorbed onto the surface of the monolayer.

18. The method according to claim 13, wherein the electrode with a cationic surface is an electrode on which a monolayer of a thiol, disulfide or sulfide compound having an cationic functional group at the terminal or a silanising agent having a cationic functional group at the terminal is formed, an anionic polymer is adsorbed onto the surface of the monolayer and a cationic polymer is further adsorbed onto its surface.

19. The method according to claim 13, wherein the electrode with a cationic surface is a transparent electrode on which a cationic polymer is adsorbed.

20. The method according to claim 14, wherein the electrode with a cationic surface is an electrode on which a monolayer of a thiol, disulfide or sulfide compound having an anionic functional group at the terminal is formed and a cationic polymer is adsorbed onto the surface of the monolayer.

21. The method according to claim 14, wherein the electrode with a cationic surface is an electrode on which a monolayer of a thiol, disulfide or sulfide compound having an cationic functional group at the terminal or a silanising agent having a cationic functional group at the terminal is formed, an anionic polymer is adsorbed onto the surface of the monolayer and a cationic polymer is further adsorbed onto its surface.

22. The method according to claim 14, wherein the electrode with a cationic surface is a transparent electrode on which a cationic polymer is adsorbed.

* * * * *

UNITED STATES PATENT AND TRADEMARK OFFICE
CERTIFICATE OF CORRECTION

| | |
|---|---|
| PATENT NO. | : 7,846,731 B2 |
| APPLICATION NO. | : 10/572920 |
| DATED | : December 7, 2010 |
| INVENTOR(S) | : Hiroo Iwata et al. |

Page 1 of 1

It is certified that error appears in the above-identified patent and that said Letters Patent is hereby corrected as shown below:

TITLE PAGE
Section (54) "Method of Introducing Nucelic Acid" should read -- Method of Introducing Nucleic Acid --.

Column 1
Line 1, "Method of Introducing Nucelic Acid" should read -- Method of Introducing Nucleic Acid --.

Column 2
Line 45, "themicroscopic" should read -- the microscopic --.

Column 3
Line 44, "acid group" should read -- acid --.

Column 7
Line 9, "urearesin, epoxyresin" should read -- urea resin, epoxy resin --.

Column 8
Line 2, "1" should read -- an integer of 1 --.

Column 12
Line 42, "pulses (A)" should read -- pulses --.

Column 13
Line 43, "4° C." should read -- 4° C --.

Equation 1
"Survival rate (%)" should read -- Survival rate (%) = --.

Signed and Sealed this
Fifth Day of July, 2011

David J. Kappos
*Director of the United States Patent and Trademark Office*